US011839702B2

(12) United States Patent
Maitland et al.

(10) Patent No.: US 11,839,702 B2
(45) Date of Patent: Dec. 12, 2023

(54) VASCULAR PROSTHESIS FOR LEAK PREVENTION DURING ENDOVASCULAR ANEURYSM REPAIR

(71) Applicants: THE TEXAS A&M UNIVERSITY SYSTEM, College Station, TX (US); SHAPE MEMORY MEDICAL, INC, Santa Clara, CA (US)

(72) Inventors: Duncan J. Maitland, College Station, TX (US); Todd L Landsman, San Jose, CA (US); John Horn, Bryan, TX (US); Landon Nash, Sunnyvale, CA (US); Chung Yeh, San Mateo, CA (US)

(73) Assignees: The Texas A&M University System, College Station, TX (US); SHAPE MEMORY MEDICAL, INC., Santa Clara, CA (US)

( * ) Notice: Subject to any disclaimer, the term of this patent is extended or adjusted under 35 U.S.C. 154(b) by 0 days.

(21) Appl. No.: 17/749,270

(22) Filed: May 20, 2022

(65) Prior Publication Data

US 2022/0273852 A1 Sep. 1, 2022

Related U.S. Application Data

(63) Continuation of application No. 16/690,612, filed on Nov. 21, 2019, now Pat. No. 11,338,070, which is a
(Continued)

(51) Int. Cl.
*A61F 2/945* (2013.01)
*A61B 17/12* (2006.01)
(Continued)

(52) U.S. Cl.
CPC ...... *A61L 31/146* (2013.01); *A61B 17/12113* (2013.01); *A61B 17/12118* (2013.01);
(Continued)

(58) Field of Classification Search
CPC ........ A61B 17/12022; A61B 17/12109; A61B 17/12113; A61B 17/12118;
(Continued)

(56) References Cited

U.S. PATENT DOCUMENTS 3,171,820 A 3/1965 Volz
5,823,198 A 10/1998 Jones et al.
(Continued)

FOREIGN PATENT DOCUMENTS

CN 104887279 A 9/2015
JP 2007021197 A 2/2007
(Continued)

OTHER PUBLICATIONS

Chinese Patent Office, Notice of Reexamination dated Oct. 19, 2022 in Chinese Patent Application No. 201880033003.1 (15 pages).
(Continued)

*Primary Examiner* — Ryan J. Severson
(74) *Attorney, Agent, or Firm* — TROP, PRUNER & HU, P.C.

(57) ABSTRACT

An embodiment includes a process for treating an abdominal aortic aneurysm (AAA) endoleak with a shape memory polymer (SMP) foam device. First, a bifurcated stent graft is placed within the aneurysm while a micro guidewire is positioned within the aneurysm for future catheter access. Second, after placing the iliac graft extension, a catheter is introduced over wire to deliver embolic foams. Third, embolic foams expand and conform to the aneurysm wall. Fourth, embolic foams create a stable thrombus to prevent endoleak formation by isolating peripheral vessels from the aneurysm volume.

20 Claims, 11 Drawing Sheets

Related U.S. Application Data continuation of application No. 16/228,082, filed on Dec. 20, 2018, now Pat. No. 10,485,903.

(60) Provisional application No. 62/609,268, filed on Dec. 21, 2017.

(51) Int. Cl.

| | | |
|---|---|---|
| *A61L 31/14* | (2006.01) | |
| *A61F 2/954* | (2013.01) | |
| *A61F 2/07* | (2013.01) | |
| *A61L 31/06* | (2006.01) | |
| *A61L 31/18* | (2006.01) | |
| *A61F 2/82* | (2013.01) | |
| *A61B 90/00* | (2016.01) | |
| *A61B 17/00* | (2006.01) | |
| *A61F 2/89* | (2013.01) | |

(52) U.S. Cl.
CPC .......... *A61B 17/12181* (2013.01); *A61F 2/07* (2013.01); *A61F 2/945* (2013.01); *A61F 2/954* (2013.01); *A61L 31/06* (2013.01); *A61L 31/18* (2013.01); *A61B 2017/00004* (2013.01); *A61B 2017/00871* (2013.01); *A61B 2090/3966* (2016.02); *A61F 2/89* (2013.01); *A61F 2002/077* (2013.01); *A61F 2002/826* (2013.01); *A61F 2210/0023* (2013.01); *A61F 2250/0098* (2013.01); *A61L 2400/04* (2013.01); *A61L 2400/16* (2013.01)

(58) Field of Classification Search
CPC ...... A61B 17/32053; A61B 17/320783; A61B 17/3478; A61B 2017/00247; A61B 2017/00309; A61B 2017/1205; A61B 2090/3966; A61M 29/00; A61F 2/07; A61F 2/945; A61F 2/954; A61L 1/18; A61L 31/06; A61L 31/146
See application file for complete search history.

(56) References Cited

U.S. PATENT DOCUMENTS

| | | | |
|---|---|---|---|
| 6,165,193 | A | 12/2000 | Greene, Jr. et al. |
| 6,238,403 | B1 | 5/2001 | Greene, Jr. et al. |
| 6,299,619 | B1 | 10/2001 | Greene, Jr. et al. |
| 6,723,108 | B1 | 4/2004 | Jones et al. |
| 6,730,119 | B1 | 5/2004 | Smalling |
| 7,530,988 | B2 | 5/2009 | Evans et al. |
| 7,666,220 | B2 | 2/2010 | Evans et al. |
| 7,744,583 | B2 | 6/2010 | Seifert et al. |
| 8,048,145 | B2 | 11/2011 | Evans et al. |
| 8,133,256 | B2 | 3/2012 | Wilson et al. |
| 8,449,592 | B2 | 5/2013 | Wilson et al. |
| 8,771,294 | B2 | 7/2014 | Sepetka et al. |
| 8,840,641 | B2 | 9/2014 | Miles et al. |
| 8,882,786 | B2 | 11/2014 | Bearinger et al. |
| 8,945,199 | B2 | 2/2015 | Ganpath et al. |
| 8,974,487 | B2 | 3/2015 | Connor et al. |
| 9,039,733 | B2 | 5/2015 | Wilson et al. |
| 9,051,411 | B2 | 6/2015 | Wilson et al. |
| 9,078,738 | B2 | 7/2015 | Wilson et al. |
| 9,561,096 | B2 | 2/2017 | Kim et al. |
| 9,597,085 | B2 | 3/2017 | Wilson et al. |
| 9,662,119 | B2 | 5/2017 | Ortega et al. |
| 9,861,517 | B2 | 1/2018 | Pavcnik et al. |
| 10,010,327 | B2 | 7/2018 | Wilson et al. |
| 10,028,747 | B2 | 7/2018 | Connor |
| 10,080,642 | B2 | 9/2018 | Wilson et al. |
| 10,136,897 | B2 | 11/2018 | Watson et al. |
| 2002/0026217 | A1 | 2/2002 | Baker et al. |
| 2002/0065542 | A1 | 5/2002 | Lax et al. |
| 2002/0169497 | A1 | 11/2002 | Wholey et al. |
| 2003/0014075 | A1 | 1/2003 | Rosenbluth et al. |
| 2003/0051735 | A1 | 3/2003 | Pavcnik et al. |
| 2003/0204246 | A1 | 10/2003 | Chu et al. |
| 2005/0043585 | A1 | 2/2005 | Datta et al. |
| 2005/0075405 | A1 | 4/2005 | Wilson et al. |
| 2005/0267570 | A1 | 12/2005 | Shadduck |
| 2006/0116709 | A1 | 6/2006 | Sepetka et al. |
| 2007/0135907 | A1 | 6/2007 | Wilson et al. |
| 2007/0150041 | A1 | 6/2007 | Evans et al. |
| 2011/0137405 | A1 | 6/2011 | Wilson et al. |
| 2011/0144686 | A1 | 6/2011 | Wilson et al. |
| 2011/0276078 | A1 | 11/2011 | Rao et al. |
| 2012/0158034 | A1 | 6/2012 | Wilson et al. |
| 2012/0265287 | A1 | 10/2012 | Sharma et al. |
| 2013/0089576 | A1 | 4/2013 | Maitland et al. |
| 2013/0253634 | A1 | 9/2013 | Wilson et al. |
| 2014/0135810 | A1 | 5/2014 | Divino et al. |
| 2014/0277057 | A1 | 9/2014 | Ortega et al. |
| 2014/0296358 | A1 | 10/2014 | Maitland et al. |
| 2015/0119706 | A1 | 4/2015 | Lu et al. |
| 2015/0257764 | A1 | 9/2015 | Wilson et al. |
| 2015/0313606 | A1 | 11/2015 | Wilson et al. |
| 2016/0022270 | A1 | 1/2016 | Watson et al. |
| 2016/0270961 | A1 | 9/2016 | Maitland et al. |
| 2017/0043512 | A1 | 2/2017 | Rodriguez et al. |
| 2017/0181750 | A1 | 6/2017 | Wilson et al. |
| 2017/0252045 | A1 | 9/2017 | Ortega et al. |
| 2018/0140304 | A1 | 5/2018 | Hasan et al. |
| 2018/0263631 | A1 | 9/2018 | Wilson et al. |
| 2019/0021838 | A1 | 1/2019 | Wilson et al. |

FOREIGN PATENT DOCUMENTS

| | | | |
|---|---|---|---|
| WO | 2016200829 | A1 | 12/2016 |
| WO | 2017040918 | A1 | 3/2017 |
| WO | 2018102779 | A1 | 6/2018 |

OTHER PUBLICATIONS

Singhal, et al., "Controlling the Actuation Rate of Low-Density Shape-Memory Polymer Foams in Water", Macromolecular Chemistry and Physics, Macromolecular Journals, 2013, pp. 1204-1214, vol. 214, Wiley-VCH Verlag Gmbh & Co., KGaA, Weinheim.

Nash, et al., "Increased X-Ray Visualization of Shape Memory Polymer Foams by Chemical Incorporation of Iodine Motifs", Polymers, Aug. 20, 2017, pp. 1-16, vol. 9, Issue 381, MDPI, Basel, Switzerland.

Rhee, et al., "Treatment of type II endoleaks with a novel polyurethane thrombogenic foam: Induction of endoleak thrombosis and elimination of intra-aneurysmal pressure in the canine model", Journal of Vascular Surgery, Aug. 2005, pp. 321-328, vol. 42, No. 2, The Society for Vascular Surgery.

Massimiliano, et al., "Embo-EVAR: A Technique to Prevent Type II Endoleak? A Single-Center Experience", Annals of Vascular Surgery, Oct. 2017, pp. 119-127, vol. 44, Elsevier Inc.

Metcalfe, et al. "Cold hibernated elastic memory foams for endovascular interventions", Biomaterials, 2002, pp. 491-497, vol. 24, Elsevier Science Ltd.

Carley, et al., Whittington's Dictionary of Plastics—Third Edition, 1993, 4 pages, Technomic Publishing Company, Inc., Lancaster, Penn., U.S.

Van Der Burg, et al. "On the Linear Elastic Properties of Regular and Random Open-Cell Foam Models", Journal of Cellular Plastics, Jan. 1997, pp. 31-54, vol. 33, Technomic Publishing Company, Inc.

"Reticulated Polyurethane Foam", Process Foam Reticulation—FXI Innovations, 2015, three pages, http://fxi.com/foam-technologies/processes/reticulation.php.

Stevens, "Chemistry of Industrial Polymers", Britannica Online Encyclopedia, 2016, 11 pages, https://www.britannica.com/topic/industrial-polymer-chemistry-468716.

The International Searching Authority, "Notification of Transmittal of the International Search Report and the Written Opinion of the International Searching Authority" dated Mar. 29, 2019 in International Application No. PCT/US2018/066919, 15 pages.

(56) References Cited

OTHER PUBLICATIONS

Chinese Patent Office, Office Action dated Mar. 29, 2020 in Chinese Patent Application No. 201880033003.1 (13 pages).
Chinese Patent Office, Office Action dated Aug. 27, 2020 in Chinese Patent Application No. 201880033003.1 (33 pages).
Chinese Patent Office, Office Action dated Feb. 19, 2021 in Chinese Patent Application No. 201880033003.1 (22 pages).
European Patent Office, Search Report dated Dec. 17, 2020 in European Patent Application No. 18890574.9 (8 pages).
European Patent Office, Office Action dated Nov. 5, 2021 in European Patent Application No. 18890574.9 (8 pages).
Japanese Patent Office, Office Action dated Mar. 27, 2020 in Japanese Patent Application No. 2019-554687 (5 pages).
Japanese Patent Office, Office Action dated Sep. 29, 2020 in Japanese Patent Application No. 2019-554687 (8 pages).
Japanese Patent Office, Office Action dated Jan. 29, 2021 in Japanese Patent Application No. 2019-554687 (8 pages).
Chinese Patent Office, Reexamination Decision dated Jun. 29, 2023 in Chinese Patent Application No. 201880033003.1 (38 pages).
European Patent Office, Communication Pursuant to Article 94(3) EPC dated Jul. 20, 2022 in European Patent Application No. 18890574.9 (7 pages).
Chinese Patent Office, Reexamination Notice dated Mar. 6, 2023 in Chinese Patent Application No. 201880033003.1 (24 pages).
Japanese Patent Office, Notice of Reason(s) for Rejection dated Oct. 18, 2022 in Japanese Patent Application No. 2021-150139 (11 pages).
Japanese Patent Office, Notice of Reasons for Rejection dated Jun. 20, 2023 in Japanese Patent Application No. 2021-150139 (6 pages).

VASCULAR PROSTHESIS FOR LEAK PREVENTION DURING ENDOVASCULAR ANEURYSM REPAIR

CROSS-REFERENCE TO RELATED APPLICATION

This application is a continuation of U.S. patent application Ser. No. 16/690,612, filed Nov. 21, 2019, which is a continuation of U.S. patent application Ser. No. 16/228,082, filed Dec. 20, 2018, now U.S. Pat. No. 10,485,903, issued Nov. 26, 2019, which claims priority to U.S. Provisional Patent Application No. 62/609,268 filed on Dec. 21, 2017 and entitled "Shape Memory Polymer Foams for Endoleak Prevention During Endovascular Aneurysm Repair." The content of each of the above applications is hereby incorporated by reference.

TECHNICAL FIELD

Embodiments of the invention are in the field of prosthesis (e.g., artificial body members) such as, for example, an arterial prosthesis.

BACKGROUND

Endovascular aneurysm repair (EVAR) is a technology for treating abdominal aortic aneurysms (AAA), wherein a stent graft is deployed to exclude the aneurysm from systemic circulation. However, common complications associated with EVAR treatments include endoleaks (blood flow outside the stent graft) and graft migration, both of which require frequent follow-up due to the risk of aneurysm growth and potential rupture. Should endoleaks occur, they may require reintervention with embolic materials to occlude the source of the endoleak.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
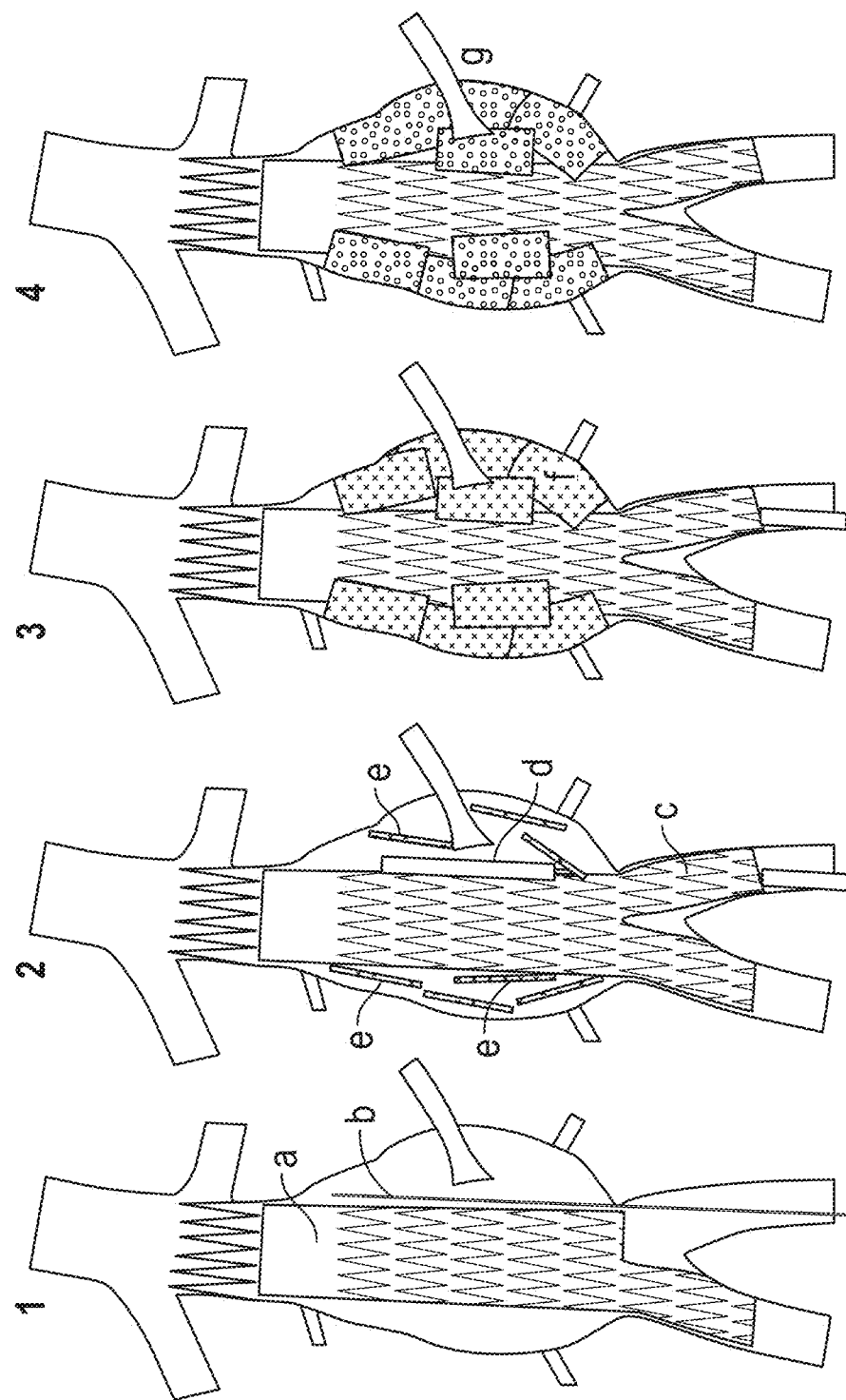
FIG. 1 depicts four stages of a process in an embodiment.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner "Connected" may indicate elements are in direct physical or electrical contact with each other and "coupled" may indicate elements co-operate or interact with each other, but they may or may not be in direct physical or electrical contact. Phrases such as "comprising at least one of A and B" include situations with A, B, or A and B.

In the past embolic materials have been investigated as suitable options for aneurysm embolization and endoleak prevention. However, Applicant determined the elastic expansion force of such materials against the catheter wall generates significant device friction during delivery. The increase in device friction leads to stiffer delivery wires, less tactile feedback during deployment, and a decrease in volumetric filling. Applicant also determined that additional materials that have been investigated for prevention of endoleaks have limitations with regard to device surface area, volume, and thrombogenicity, which leads to numerous devices being required to fill the aneurysmal space and prolonged treatment times.

In contrast, embodiments described herein include a polyurethane shape memory polymer (SMP) foam that functions as an effective embolization device with favorable healing responses and relatively low friction during delivery due to the shape memory effect. These foam devices are capable of volume expansions of up to 70× or more to provide efficient volumetric filling without generating significant pressure on the aneurysm wall and can be delivered through tortuous pathways with low friction via catheterization. Such foam embodiments function as an embolic agent and subsequent scaffold for a healthy healing response, which makes them ideal for a catheter delivered whole foam devices for endoleak prevention during EVAR.

Applicant further determined the advantage of providing visibility for the entire foam length. For this reason, embodiments include radiopaque SMP foam formulations designed for X-ray visibility, as well as alternative means of visualizing the entire foam length. These alternative means of visualization include the use of a radiopaque fiber or coil that extends through the core and spans the entire device length. The termination point of the radiopaque fiber or coil corresponds to the distal and/or proximal tip of the SMP foam to indicate where one or both ends of the device are located. Alternatively, a radiopaque marker band may be used on one or both of the proximal and distal ends of the device to indicate where both ends of the device are located under X-ray.

Applicant further determined previously known SMP foam chemistries are inherently oxidatively degraded during the healing process in vivo by macrophages and neutrophils. However, certain embolization indications benefit from a permanent, compliant scaffold, like an SMP foam, since the risk of recanalization may increase if the embolic material degrades prior to complete healing in the body. Additionally, certain indications, such as AAA's and endoleaks may require very large volumes of SMP foams to be implanted to effectively treat the patient. In these large volumes, degradation byproducts may cause unknown complications due to the large concentration of compounds in one region subjected to slow clearance rates. Due to these risks of recanalization and potential toxic byproducts, embodiments include a biodurable, or non-degradable, SMP foam formulation for use in these indications which require large volumes of permanent embolic materials.

Broader Impacts

Applicants determined there is a medical need for a technology that will reduce the number of endoleaks, secondary interventions, and monitoring of patients who have undergone EVAR for AAA's. SMP foam embodiments for perigraft embolization of AAA's provide a safe and effective means to mitigate the occurrence of EVAR complications. The embolization device embodiments described herein save patients thousands of dollars in post-EVAR management, prevent life-threatening complications, and have an impact on the healthcare industry through reimbursement based on superior clinical outcomes.

General

Embodiments take a materials science approach to address the unmet clinical need of endoleak treatment and prevention. This is accomplished through thermomechanical optimization of SMPs. The embodiments address, for example:

Optimized SMP foam morphology, expansion behavior, expanded device geometry, and delivery platform that enables consistent device delivery through 5-9F catheters and sheaths.

Verified device delivery, device expansion, and perigraft flow stasis within an EVAR treated AAA benchtop flow model with simulated endoleak.

Device Safety and Efficacy.

Thus, embodiments prove the feasibility of the AAA embolic foam device in vitro and in vivo. Embodiments are viable adjuncts to endovascular aneurysm repair procedures as a prophylactic against endoleak formation.

Significance

Until the past decade, the traditional method of AAA repair was open surgery, but since 2006, EVAR has been preferred to open surgical repair, accounting for 74% of all AAA treatments. Although open surgery repair and EVAR have similar long term survival rates of 69.9% and 68.9%, respectively, the procedural preference for EVAR is motivated by shorter hospital stays, less blood loss, shorter operating times, and lower early morbidity and mortality. Despite the advantages of EVAR, as high as 32% of the 33,000 annual EVAR procedures in the US can still result in some type of endoleak. Endoleak, as used herein, is defined as blood flow outside of the stent graft but within the aneurysm sac, which can result in aneurysm enlargement and rupture. The origin of the leak defines the type of endoleak, but all or most types are typically monitored with long term surveillance or addressed with subsequent surgical procedures. New endoleaks have developed as long as several years post procedure, which necessitates long term patient screening.

As more patients are opting for EVAR, there is a strain on healthcare systems to cover the cost. Long-term surveillance, imaging studies, and reintervention have been shown to increase the global cost of EVAR by nearly 50%. According to recent meta-analyses, EVAR has a 56% greater intermediate reintervention rate and 243% greater long-term reintervention rate when compared to open surgical repair. Despite more compliant stent-graft technology and more surgical experience, EVAR remains less durable than open repair. Long-term durability of EVAR suffers due to endoleak development, graft migration, and continued sac pressurization, all of which may result in sac rupture. Despite new technology for stent-grafts, the amount of people who develop endoleaks has not significantly decreased, partly as a result of endografts being implanted outside of their instructions for use (IFU) and the inability to effectively prevent type II endoleaks.

Embodiments help prevent or mitigate endoleaks and may liberalize the IFU for stent-grafts, reduce EVAR complications related to endoleak, and reduce the amount of stringent post-EVAR imaging. The benefits of such embodiments will have a positive impact economically, physically, and mentally on patients due to increased EVAR durability and reduced monitoring. Accordingly, embodiments that reduce the development and severity of endoleaks will improve cost effectiveness and durability of EVAR.

Type I (T1) and type III (T3) endoleaks have been treated by coil embolization, angioplasty, additional endografts, or glue embolization. However, management for type II (T2) endoleaks remains controversial despite being the most common type of endoleak. Unlike T1 and T3 endoleaks, T2 endoleaks can spontaneously resolve and their relationship to aneurysm sac enlargement and pressurization are uncertain. There is a consensus, however, that persistent T2 endoleaks (>6 months) are associated with aneurysm sac growth, reintervention, conversion to open repair, and rupture. Furthermore, the detection and embolization of T2 endoleaks is difficult due to the size of feeding vessels. As a result of inadequate detection of endoleaks and the ability of endoleaks to resolve then reappear, patients are monitored yearly. Regardless of the type of endoleak, embodiments address a clinical need to make EVAR more durable and to exclude the aneurysm from systemic circulation. Sac embolization at the time of EVAR has been studied in an effort to reduce endoleak development. These prophylactic embodiments reduce the need for long-term surveillance, prevent endograft migration via biological fixation, and mitigate endoleak formation. Embodiments utilize SMP materials that have advantages over more conventional materials. Those advantages relate to, for example, cytotoxicity, potential to create colonic ischemia, insufficient control and predictability, difficult delivery, incomplete occlusion, and recanalization.

Expandable polyurethane foam embodiments are used in embodiments due to their excellent acute thrombogenicity, long term biocompatibility, tunable pore size, and favorable healing response. Polyurethane SMP foam embodiments are used in catheter-based embolic devices because they can deform into a secondary shape for delivery purposes, and subsequently actuate to their primary shape using stimuli such as heat. Embodiments leverage the ability of polyurethane SMPs to thermally expand at body temperature after being delivered via catheterization to treat and prevent endoleaks, as well as to mitigate complications of EVAR. Embodiments enable development of therapeutic and preventative treatments of AAA to lessen the burden of long-term monitoring, secondary intervention, and lifetime cost of EVAR.

Embodiments include ultra-low density SMP polyurethane foams with customizable glass transition temperatures, 98% shape recovery, a glassy storage modulus of 200-300 kPa, and recovery stresses of 5-15 kPa. These materials are synthesized from low-molecular weight branched monomers, and undergo foaming to create highly chemically crosslinked, highly porous, low density network structures. This high crosslink density prevents "secondary-shape forming" from occurring in the SMP polyurethane foams, which preserves the primary shape and improves the shelf life of the device by reducing the likelihood of chain relaxation. The foams also have porosities as high as 98.8%, which allow the foams to serve as a scaffold for tissue ingrowth and enables greater volumetric expansions when compared to neat SMPs. Further, the interconnected porous geometry of the material improves embolization by promoting flow stasis and providing a large surface area to trigger the intrinsic clotting cascade.

FIG. 1 outlines an embodiment of a process for treating AAA endoleak with whole SMP foam devices. At stage 1 a bifurcated stent graft (a) is placed within the aneurysm while a micro guidewire (b) is positioned within the aneurysm for future catheter access. At stage 2, after placing the iliac graft extension (c), a 5F catheter (d) is introduced over wire (b) to deliver embolic foams (e). At stage 3 embolic foams expand and conform to the aneurysm wall (f). At stage 4 embolic foams create a stable thrombus to prevent endoleak formation by isolating peripheral vessels (g) from the aneurysm volume.

Despite SMP foam low density and lack of inherent X-ray attenuation, embodiments of SMP polyurethanes are made radiopaque through the incorporation of tungsten particles into the polymer structure. By loading 4% by volume of tungsten into SMP foams, radio-opacity is achieved while maintaining favorable mechanical, morphological, and chemical properties of unloaded foams. Solid polymer, polymer foams, and crimped foams of different geometries were mounted to a porcine head to mimic the density of a human skull and were imaged under fluoroscopy. Doped SMP with 4% by volume tungsten were visible under fluoroscopy. More specifically, 4% tungsten-doped SMP cylinders of various mm thicknesses imaged via fluoroscopy with a pig's skull providing relative radio opacity. The cylinders were visible.

Additionally, tungsten doped SMP foams were implanted into a vein pouch porcine aneurysm model and resulted in dense cellular connective tissue infiltrating the foam with minimal inflammation. When viewed under scanning electron microscopy (SEM), tungsten particles were encapsulated in polymer matrix that remained intact after 90 days in vivo, suggesting non-toxic leaching. Tensile testing of non-loaded foams compared with tungsten loaded foams showed an increase in toughness and 43% increase in modulus. SEM images showed greater cell density as a result of tungsten particles, which contributes to the increased stiffness of the foams. Finally, glass transition temperatures did not change significantly with the addition of tungsten. The results from these investigations emphasize the clinical feasibility of embodiments to be delivered safely into an AAA sac under fluoroscopy while maintaining favorable volumetric expansion and biocompatibility.

Embodiments demonstrate that SMP polyurethane foams are a class of materials that have unique properties adept at aneurysm filling. These materials provide an effective and safe preventative treatment against the development of endoleaks, and may reduce the long-term surveillance that is necessary for EVAR. Prophylactic treatment of AAAs could improve the long-term durability of EVAR and reduce the high number of secondary interventions many EVAR patients undergo, usually as a consequence of endoleak or graft migration. Additionally, embodiments may liberalize the instructions for use for many stent-graft procedures, allowing otherwise untreatable AAAs the ability to be repaired. The development and further characterization of SMP polyurethane foams can also be applied to many other embolic or vascular occlusion devices.

Issue 1: Embodiments optimize the SMP foam morphology, expansion behavior, expanded device geometry, and delivery platform to enable consistent device delivery through a 5F catheter.

Figure 2:
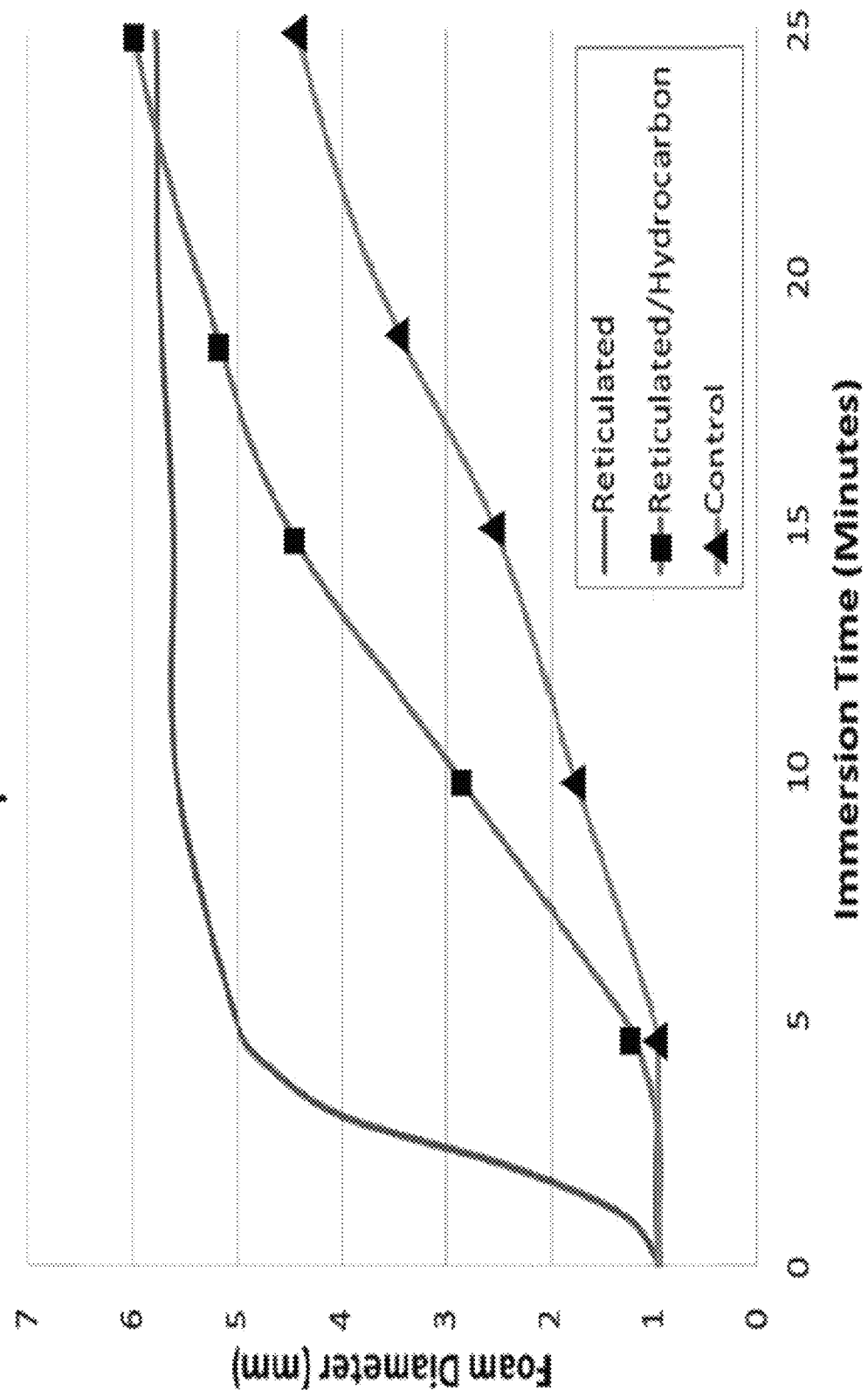
FIG. 2 depicts characteristics of various embodiments.

Embodiments provide an actuation method that has a delayed expansion using body temperature and the aqueous environment of the blood. The actuation kinetics of the foam are tailored by altering the glass transition temperature ($T_g$) relative to body temperature and altering the bulk foam hydrophobicity to control the moisture plasticization rate. Both $T_g$ and hydrophobicity are altered by varying the diisocyanate monomer ratios within the polyurethane synthesis. As shown in FIG. 2 (where at 10 min reticulated foam is highest and the control is lowest in diameter), the actuation profile of the foam can be further optimized by using cold plasma surface functionalization with two different approaches (Aurora 350, Plasma Technology Systems). First, hydrocarbon process gasses (e.g. acetylene, ethylene, propylene) deposit an aliphatic water diffusion barrier to slow the moisture plasticization rate and delay passive foam expansion. Second, oxygen and tetraflouromethane process gasses create an oxidative atmosphere to etch the polymer membranes, creating a highly reticulated foam structure with higher surface hydrophilicity, which both contribute to faster foam expansion.

More specifically, FIG. 2 shows foams with varying surface modifications display different expansion kinetics when submersed in 37° C. water. Foams were fabricated with an isocyanate ratio of 70% hexamethylene diisocyanate, 30% trimethylhexamethylene diisocyanate. The plasma reticulation atmosphere consisted of oxygen and tetraflouromethane ionized at 300 W for 30 seconds. The hydrocarbon plasma atmosphere consisted of acetylene and propylene ionized at 150 W for 2 minutes.

By tailoring the bulk hydrophobicity of the foam and the diffusion characteristics of the surface, the actuation profile of the foam is tailored for delayed expansion. Controlled delay prevents the device from deploying and binding within the delivery catheter, but still allows the foam to expand and fill the aneurysm anatomy at body temperature without an external heating source.

Figure 3:
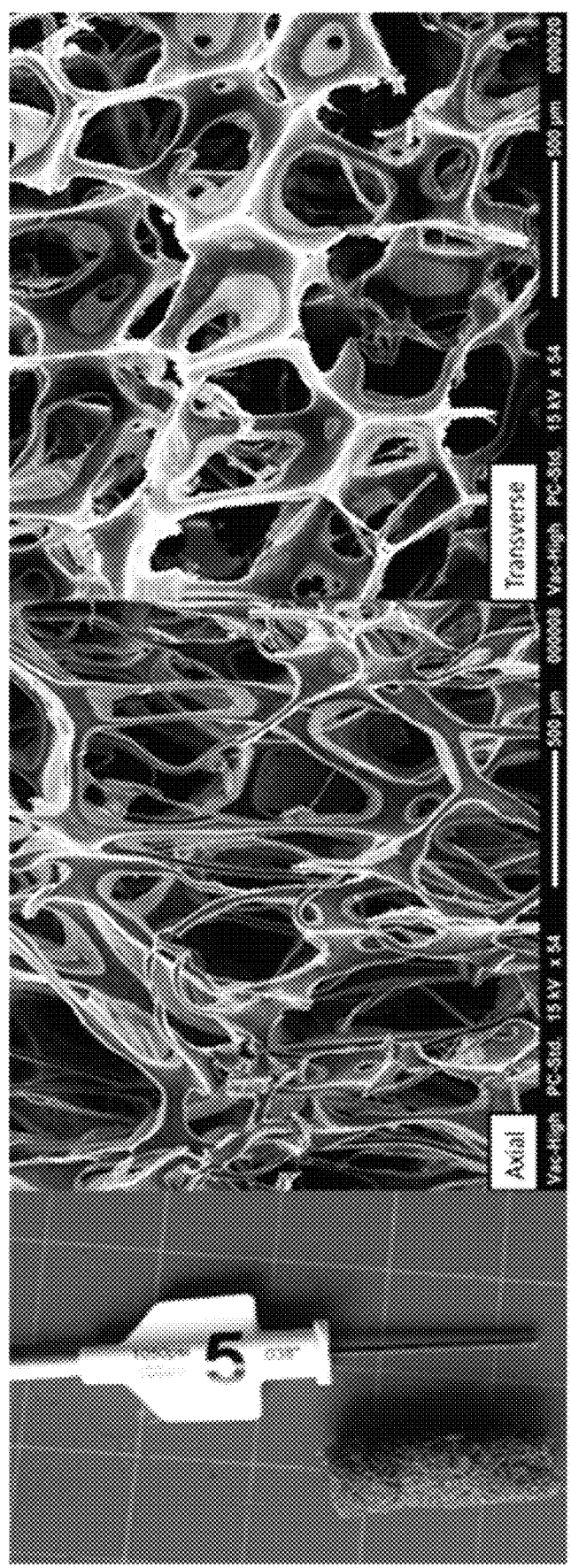
FIG. 3 shows various amplifications of foam embodiments.

FIG. 3 shows the expanded and crimped morphologies of SMP devices in various embodiments. The left panel of FIG. 3 shows a comparison between an expanded 10 mm diameter tungsten doped SMP foam device and a crimped 1.3 mm diameter SMP device loaded into a 5F catheter. SEM images show the expanded morphology of a reticulated foam along the foaming axis (axial, middle panel) and orthogonally (transverse, right panel).

A delivery platform incorporating an introducer device and delivery wire facilitate quick and safe delivery of crimped SMP devices through the catheter and into the aneurysm site. Introducer devices enable the safe removal of air from the foams through a series of flushes and hemostatic valves.

Issue 2: Embodiments verify device delivery, device expansion, and perigraft flow stasis within an EVAR treated AAA benchtop flow model with simulated endoleak.

Figure 4:
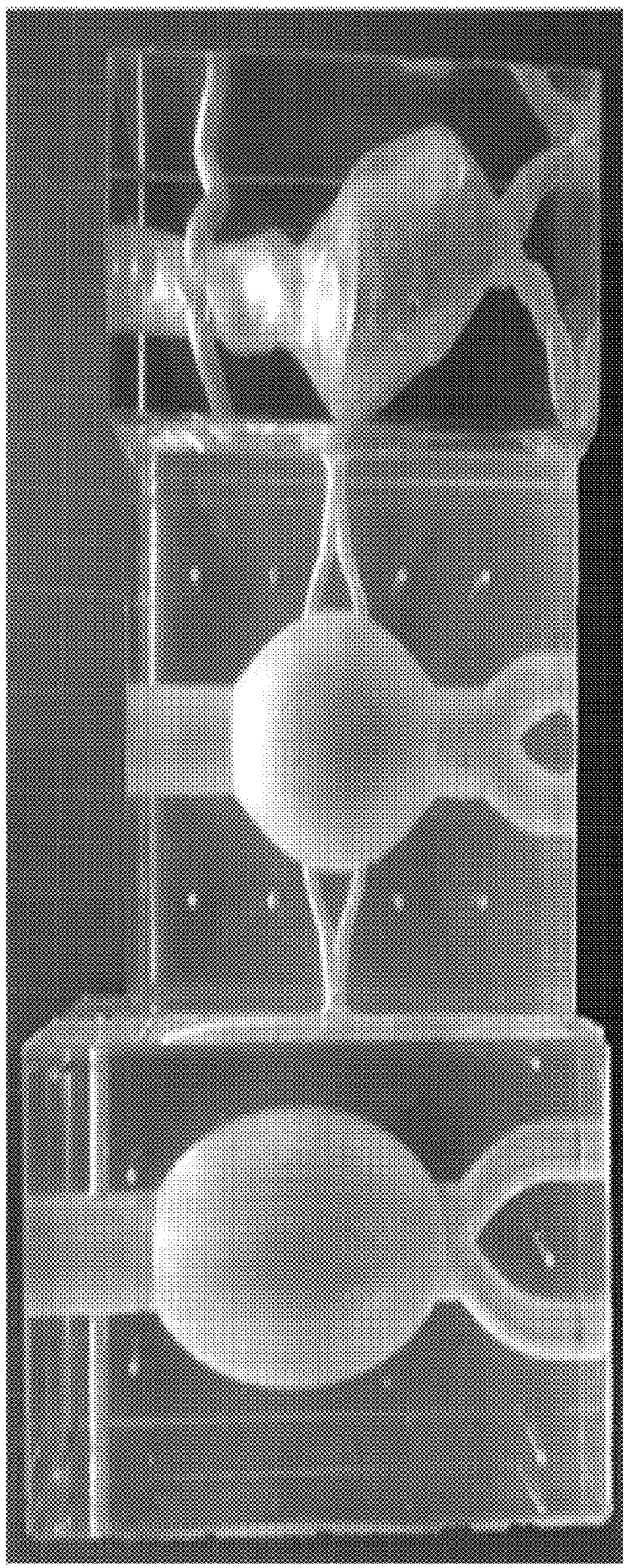
FIG. 4 shows various aneurysm shapes suitable for treatment with embodiments.

Silicone vascular phantoms representing idealized and physiologic AAA anatomies were fabricated and incorporated into flow loops at physiologic temperature. Expired EVAR grafts were placed within the phantoms with secondary flow channels providing simulated T2 endoleak flow. Graft placement was modified to simulate a T1 or T3 endoleak. FIG. 4 depicts several phantom designs. More specifically, FIG. 4 shows from left to right: Large idealized AAA model with renal arteries, idealized AAA model with collateral vessels to mimic type II endoleak, and a CT reconstructed AAA model.

SMP foam devices were delivered into the pseudo-aneurysm sac via a 5F catheter to emulate clinical delivery. Flow stasis may be quantified by the time it takes the dye to clear the aneurysm space when compared to a baseline value prior to foam implantation. This metric helps quantify the probability of sufficient flow stasis for embolization within the aneurysm and subsequent endoleak stabilization.

Issue 3: Embodiments demonstrate device safety and efficacy in a pilot animal study using a porcine AAA animal model.

Domestic swine weighing approximately 20 kilograms underwent surgery to create an aneurysm in the abdominal aorta. A vascular stent graft was deployed to isolate the surgically created abdominal aortic aneurysm, followed by the delivery of embolic foams through a 6-8F catheter to occlude the perigraft space. Three-dimensional computerized tomography angiography (3D-CTA), conventional angiography, and X-ray was performed prior to and following foam treatment to observe the presence of endoleak and determine the extent of acute embolization.

Additional Embodiments

An embodiment provides a solution to prevent endoleaks by filling the voids within sequestered regions by conforming to the contours of the scaffold/graft and the physiologic environment, creating rapid thrombus formation and obstruction of systemic blood flow, eventually leading to scar tissue formation and permanent exclusion of blood flow through the sequestered region.

The foam material utilized in an embodiment allows compression for delivery through small caliber delivery catheters with subsequent expansion in diameter or length to fill large volumes. Upon expansion, the foams induce thrombosis via flow stagnation, activation of the intrinsic clotting cascade upon blood contact with the foam material, and activation of the extrinsic clotting cascade upon foam contact with the inner surface of the vessel or aneurysm. This prevents continued blood flow through or into the sequestered region, and leads to eventual connective tissue infiltration into the foam volume or the volume previously occupied by foams and permanent healing at the site of the vascular anomaly. This strengthens the once susceptible region that was sequestered and reduces the risk of vessel injury or rupture.

The ability of foam embodiments to cause flow stagnation within the vasculature and the ability to promote significant connective tissue infiltration over time after initial thrombosis differ from prior methods. Such prior methods intended to fill the void space within a sequestered region with a material to exclude the void space and provide semi-rigid support of the surrounding environment. In contrast, the foams of embodiments conform to fill the void space within the sequestered region, remain compliant throughout the treatment lifetime, and allow the sequestered region to heal over time rather than applying constant pressure to the susceptible region. Embodiments use foams that are biodegradable or biodurable implants, and both types of foam provide a scaffold for future connective tissue infiltration while also remaining compliant to the surrounding environment.

An embodiment of SMP foam includes a 100% hexamethylenediisocyanate (HDI) foam for the isocyanate component of the polyurethane (PU) foam. However, other embodiments include 95, 90, 85, 80, 75, 70, 65, 60% or less HDI. The remainder of such foams may include isocyanate components taken from, for example, trimethylhexanediisocyanate (TMHDI) and/or isophorone diisocyanate (IPDI), and the like. The high HDI content promotes faster expansion of the foam. Embodiments may also include key ratios for polyfunctional alcohol content of the PU foam. For example, an embodiment foam may be formed from triethanolamine (TEA) and tetrakis (2-hydroxyl propyl) ethylenediamine (HPED). The ratio between these two alcohols is 80:20 to further promote rapid expansion/actuation of the foams. However, other embodiments may include ratios of 90:10, 70:30, 60:40, and 50:50 between the two alcohols and other embodiments may include other alcohols entirely.

Embodiments may include a radiopaque foam, and/or biodurable foams. The following provide examples of radiopaque and/or biodurable foams.

Example 1a includes a system comprising: a thermoset shape memory polymer (SMP) foam that is covalently bonded to iodine; wherein (a) the SMP foam is configured to expand from a compressed secondary state to an expanded primary state in response to thermal stimulus, and (b) the SMP foam is a poly(urethane-urea-amide).

Example 2a includes the system of example 1a wherein the SMP foam is radiopaque.

Example 3a includes the system of example 2a wherein the iodine is included in a triiodobenzene monomer.

Example 4a includes the system of example 3a wherein the triiodobenzene monomer includes at least one of (a) 5-amino-2,4,6-triiodoisophthalic acid (ATIPA), (b) diatrizoic acid, (c) iohexol, and (d) triiodophenol.

Example 5a includes the system of example 4a wherein the triiodobenzene monomer includes ATIPA.

Example 6a includes the system of example 5a wherein the ATIPA crosslinks polymer chains of the SMP foam.

Another version of example 6a includes the system of example 5a wherein (a) the ATIPA crosslinks polymer chains of the SMP foam, and (b) another crosslinking agent crosslinks polymer chains of the SMP foam.

Example 7a includes the system of example 3a wherein the SMP foam includes at least one of platinum, tungsten, and tantalum, the at least one of platinum, tungsten, and tantalum being physically bound within the SMP foam.

Example 8a includes the system of example 7a wherein the at least one of platinum, tungsten, and tantalum is not chemically bound to the SMP foam.

Example 9a includes the system of example 3a comprising a backbone that traverses the SMP foam, wherein the backbone includes at least one of a polymer filament and a metal.

Example 10a includes the system of example 9a wherein the backbone includes a polymer filament and no metal.

In other version of Example 10a the backbone includes a polymer but no metal. In other version of Example 10a the backbone includes a majority % of polymer and a minority % of metal.

Example 11a includes a method comprising: providing a triiodobenzene monomer; providing an aliphatic monomer comprising at least one of (a)(i) multiple amine functional groups, (a)(ii) multiple alcohol functional groups, and (a)(iii) multiple carboxylic acid functional groups; providing a diisocyanate; mixing the triiodobenzene monomer, the aliphatic monomer, and the diisocyanate into a solution; forming a thermoset shape memory polymer (SMP) foam from the solution.

Example 12a includes the method of example 11a wherein: triiodobenzene monomer includes a first member selected from the group consisting of 5-amino-2,4,6-triiodoisophthalic acid (ATIPA), diatrizoic acid, iohexol, or triiodophenol; the aliphatic monomer includes a second member selected from the group consisting of 1,2,6-hexanetriol (HT); 2-butyl-2-ethyl-propanediol (BEP); 3-methyl-1, 5-pentanediol (MPD); diethylene glycol (DEG); triethylene glycol (TEG); triethanolamine (TEA); tetrakis-hydroxypropyl ethylenediamine (HPED); glycerol; trimethylolpropane; trimethylolmethane; 1,2,4-butanetriol; 1,2-diaminopropane; 2,2-Dimethyl-1,3-propanediamine; 1,8-Diaminooctane; 3-Amino-1,2-propanediol; 2-Amino-2-methyl-1,3-propanediol; 1,3-Diamino-2-propanol; or aspartic acid; the diisocyanate includes a third member selected form the group consisting of hexamethylene diisocyanate (HDI); trimethylhexamethylene diisocyanate (TMHDI); isophorone diisocyanate; 1,3,4-triisocyanato-2,4,6-trimethylbenzene; toluene diisocyanate; or methylene diphenyl diisocyanate.

Example 13a includes the method of example 12a wherein the second member is selected from the group consisting of HT; BEP; MPD; DEG; TEG; TEA; HPED; glycerol; trimethylolpropane; trimethylolmethane; or 1,2,4-butanetriol.

Example 14a includes the method of example 12a wherein the second member is selected from the group consisting of 1,2-diaminopropane; 2,2-Dimethyl-1,3-propanediamine; 1,8-Di aminooctane; 3-Amino-1,2-propanediol; or 2-Amino-2-methyl-1,3-propanediol.

Example 15a includes the method of example 12a wherein the third member is selected form the group consisting of HDI; TMHDI; and isophorone diisocyanate.

Example 16a includes the method of example 12a wherein the third member is selected form the group consisting of elected form the group consisting of 1,3,4-triisocyanato-2,4,6-trimethylbenzene; toluene diisocyanate; or methylene diphenyl diisocyanate.

Example 17a includes the method of example 12a wherein the first member is ATIPA.

Another version of Example 17a includes the method of example 12a wherein the first member is ATIPA and the ATIPA constitutes between 20 and 30% MW of the first and second members.

Example 18a includes the method of example 12a comprising crosslinking the second and third members with the first member.

Example 19a includes the method of example 18a wherein forming the SMP foam from the solution comprises utilizing the first member as a chemical blowing agent.

Example 20a includes the method of example 12a wherein the aliphatic monomer includes a fourth selected from the group consisting of HT; BEP; MPD; DEG; TEG; TEA; HPED; glycerol; trimethylolpropane; trimethylolmethane; 1,2,4-butanetriol; 1,2-diaminopropane; 2,2-Dimethyl-1,3-propanediamine; 1,8-Di aminooctane; 3-Amino-1, 2-propanediol; 2-Amino-2-methyl-1,3-propanediol; 1,3-Di amino-2-propanol; or aspartic acid;

Example 21a includes a system comprising: an iodine containing thermoset open-cell shape memory polymer (SMP) foam that is x-ray visible; wherein (a) the SMP foam is configured to expand from a compressed secondary state to an expanded primary state in response to thermal stimulus, (b) the SMP foam is a poly(urethane-urea-amide).

Whether something is "x-ray visible" or "radiopaque" is judged according to a person of ordinary skill in the art, such as a neurosurgeon or interventional neuroradiologist that routinely treats aneurysms using imaging, such as fluoroscopy or angiography. While x-ray power may vary depending on the imaging machine used and the like, a person of ordinary skill in the art will still understand whether a foam is visible under normal clinical conditions such that the foam is discernable from the surrounding anatomy.

Example 22a includes the system of example 21a wherein the iodine is included in a triiodobenzene monomer and the iodine is covalently bonded within a polymer network of the SMP foam.

Another version of Example 22a includes the system of example 21a wherein the iodine is included in a triiodobenzene monomer and the iodine is physically incorporated within the SMP foam.

Another version of Example 22a includes the system of example 21a wherein the iodine is included in at least one triiodobenzene monomer and the iodine is both: (a) covalently bonded within a polymer network of the SMP foam, and (b) physically incorporated, but not chemically bonded, within the SMP foam.

Example 23a includes the system of example 22a wherein the SMP foam in the secondary state contains between 50 and 500 mg/ml of Iodine.

However, other embodiments the SMT foam in the secondary state may include between 50 and 100, 100 and 200, 200 and 300, 300 and 400 or more mg/ml of Iodine.

Example 24a includes the system of example 23a wherein: the SMP foam in its primary state has a density of less than 0.1 g/cc; the SMP foam has a dry glass transition temperature (Tg) between 30 and 100 degrees C.

Another version of Example 24a includes the system of example 23a wherein: the SMP foam in its primary state has a density of less than 0.1 g/cc; the SMP foam has a dry glass transition temperature (Tg) between 30 and 100 degrees C.; and the SMP foam lacks a Fourier transform infrared spectroscopy (FTIR) urea peak at 1650 cm-1.

Other versions of Example 24a have a density of less than 0.09, 0.08, 0.07, 0.06, or 0.05 g/cc.

Example 25a includes the system of example 22a wherein the SMP foam comprises polycaprolactone (PCL).

Another version of Example 25a includes the system of example 22a wherein the SMP foam comprises a hydrolytically degradable ester linkage.

Another version of Example 25a includes the system of example 22a wherein the SMP foam comprises at least one of polycaprolactone (PCL) or a different hydrolytically degradable ester linkage.

In an embodiment the graft is deployed to the region, followed by the implantation of the foams, however, the foams may also be deployed first and then kept in place by the placement of a graft. Other methods include the method of FIG. 1.

For instance, different embodiments may vary the order in which the foams could be deployed—(i.e., before or after the stent graft (or a similar scaffold) is deployed across an aneurysm or cavity). One order may be to deploy the scaffold first, and then the foams so that the scaffold keeps the foams in place. However, in a low-flow region (for example) an embodiment may have the foams deployed first and then the scaffold.

Alternative uses for embodiments may be to impart a specific shape on a graft or biologic structure by applying external or internal pressure to the walls of the graft or structure.

For instance, an embodiment may include a specific shape of foam or neat polymer. The shape may be, for example, a shape of replacement bone such as a chin or cheek bone. The SMP could be set it into an easy-to-deliver shape (e.g., columnar). A physician could then make a small incision in the skin into which the polymer is placed into a cavity in the tissue. The SMP then subsequently expands into a perfectly shaped chin or cheek bone. Thus, embodiments may be used for orthopedic or plastic surgery spaces (and many others) where one needs a scaffold to support skin in a certain way, but it also must remain compliant, which can be accomplished with SMP embodiments described herein (i.e., conform to the surroundings and remain compliant). Additionally, SMPs with higher radial forces would allow one to implant such a SMP to deflect a graft or pieces of tissue in a desired way as the foam expands from a crimped state to an expanded state.

An embodiment includes singular or multiple crimped foams with or without a core element running centrally through them loaded into an introducer that allows them to be transferred directly into a guide catheter using a guidewire or a pusher wire/rod.

FIGS. 5A-G show frames from videos. Such frames show SMP foam when utilized with a graft or scaffold.

Figure 5A:
FIGS. 5A-5G show various deployment stages and configurations in various embodiments.
Figure 5B:

Specifically, FIGS. 5A-B address a benchtop aneurysm model. FIG. 5A shows at least three foams deployed from a catheter. The foams are not coupled to each other. Each foam has a radiopaque cap on one end of the foam. A pusher rod or, more generally, a pushing element is shown emanating from a delivery conduit. The pushing element is used to push the foams out of the delivery conduit. FIG. 5B shows the foams actuating/having actuated.

Figure 5C:
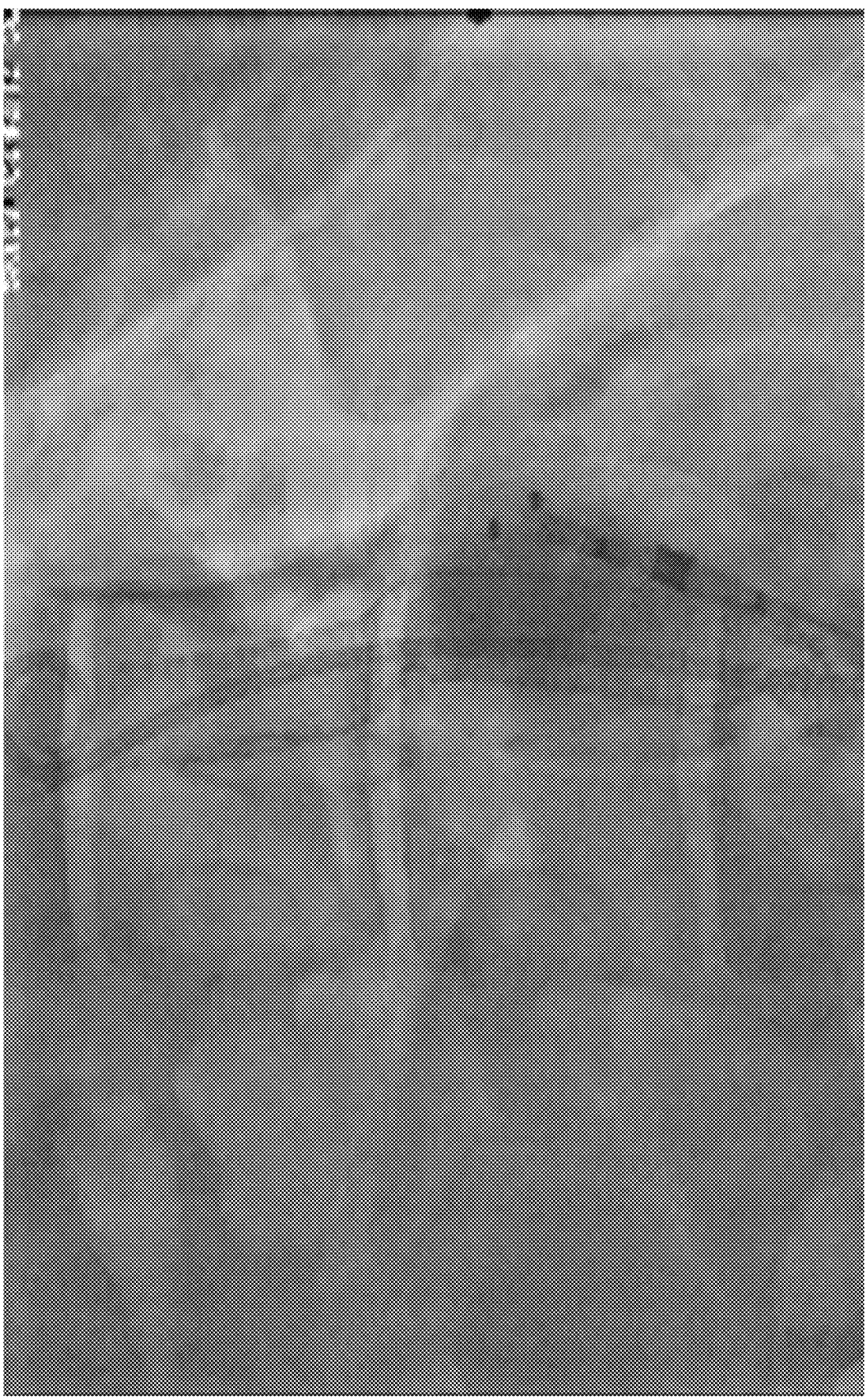
Figure 5D:
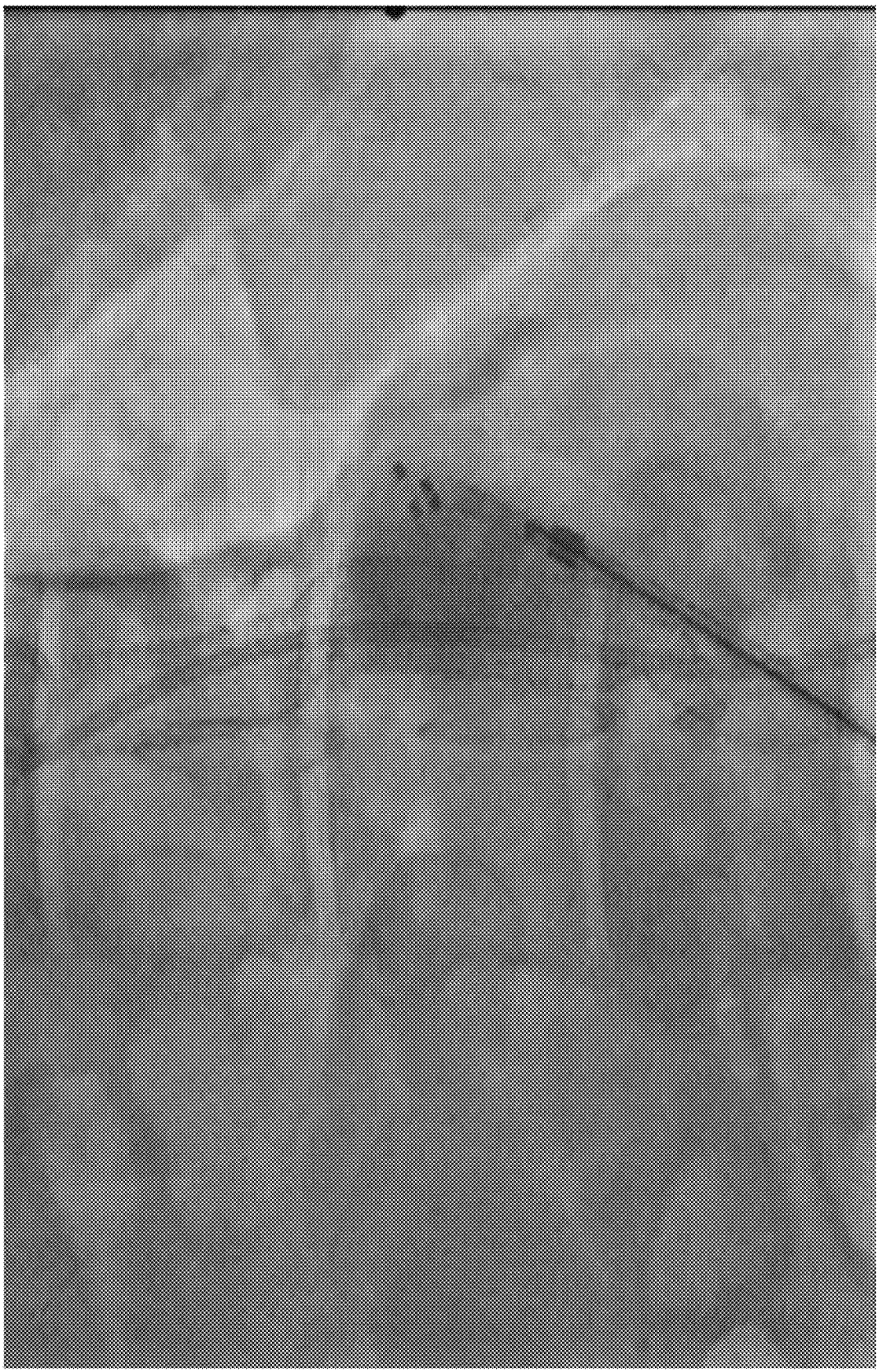
Figure 5E:
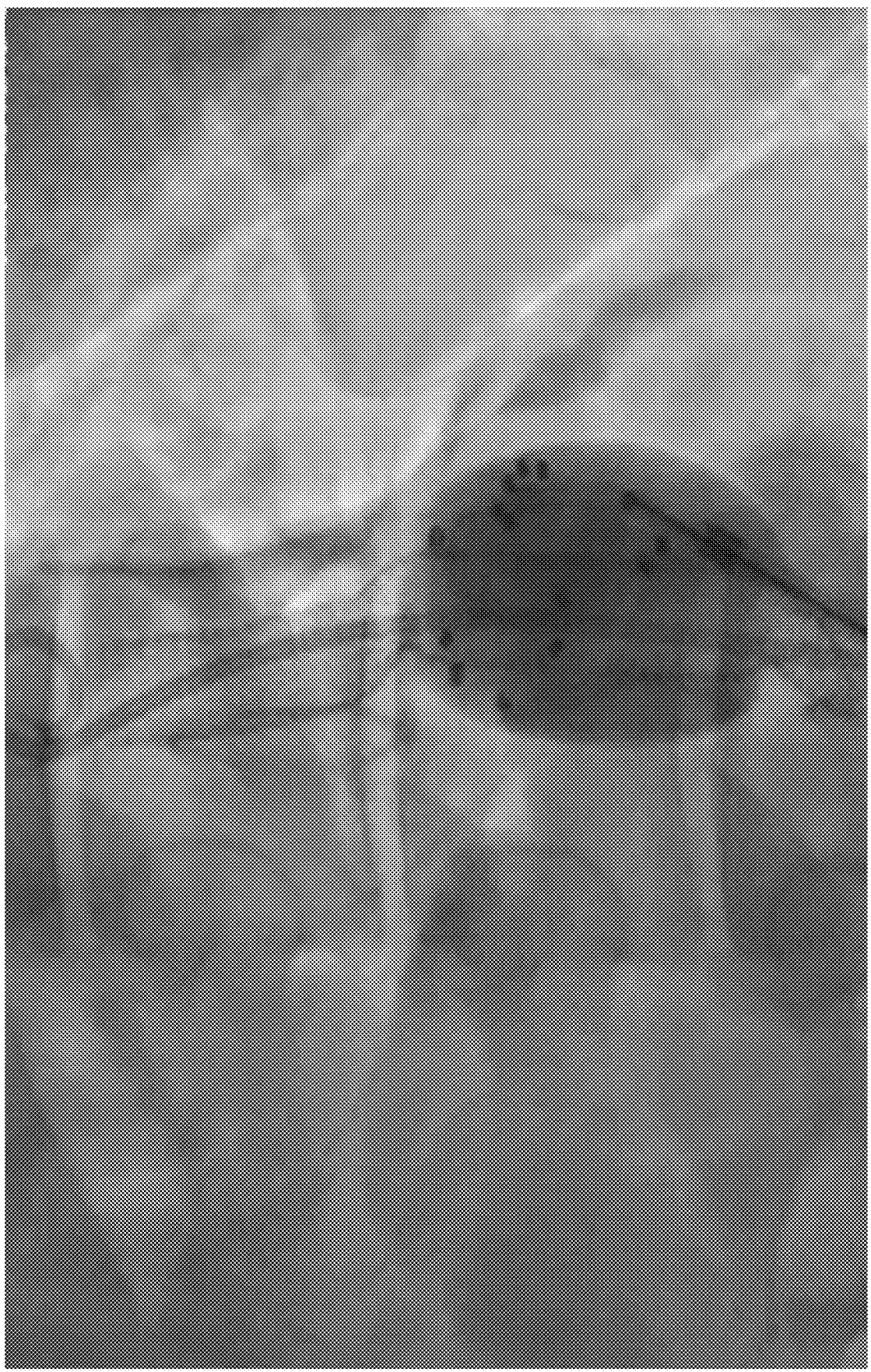
Figure 5F:
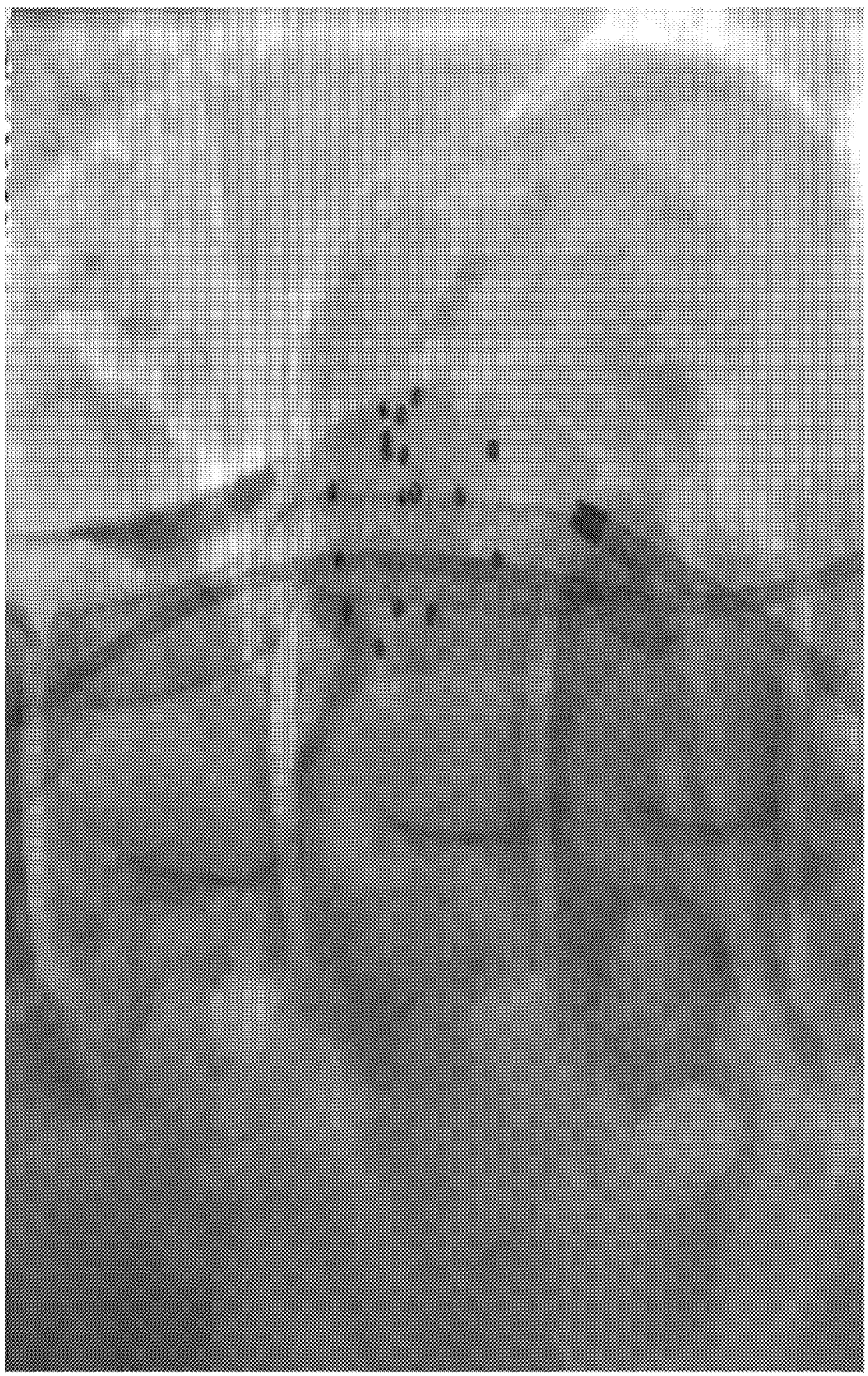
Figure 5G:
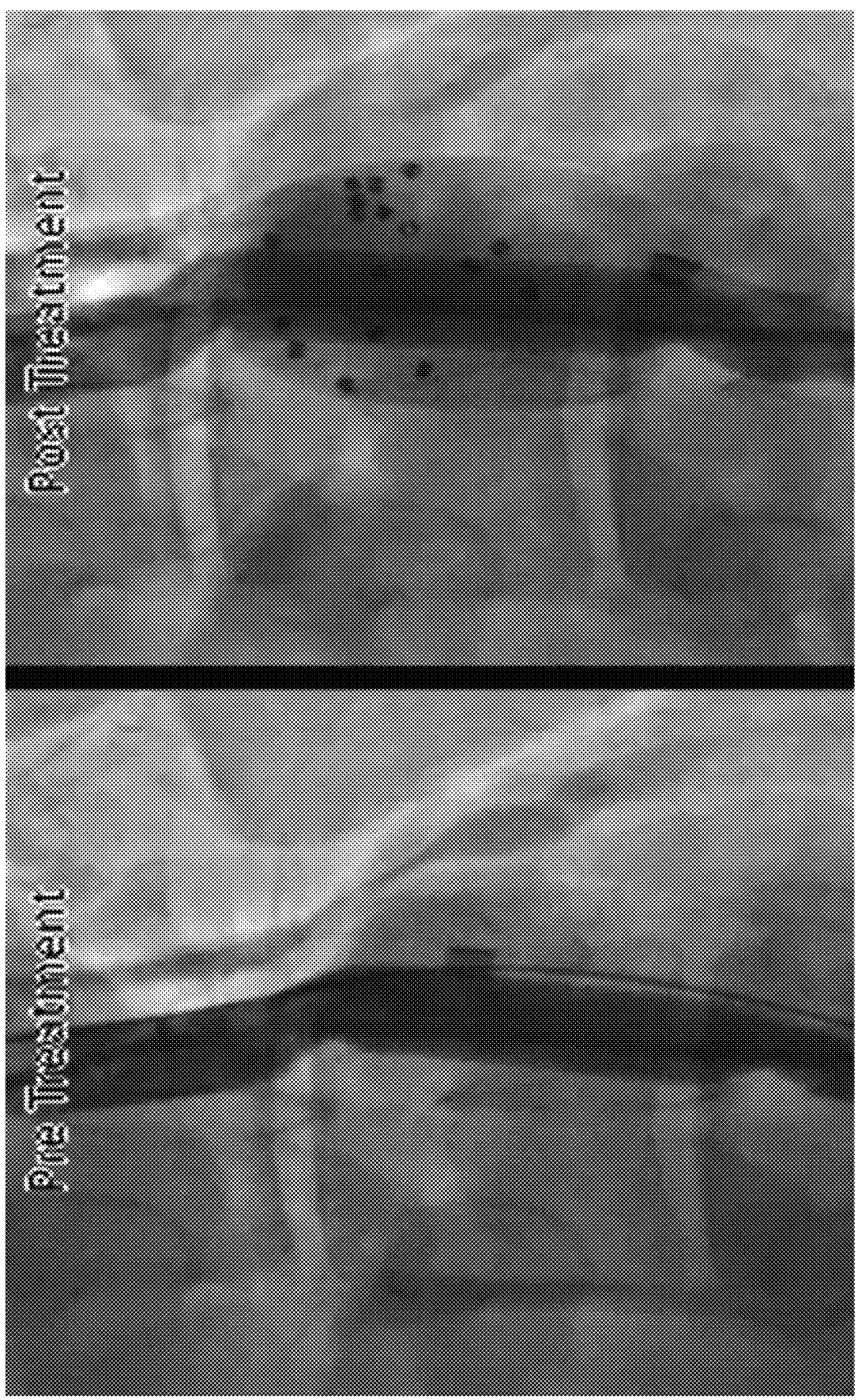

FIGS. 5C-G address a porcine aneurysm model. FIG. 5C shows two foams having been pushed out of a delivery conduit. The conduit is visible. A non-deployed foam is shown still within the conduit. Each foam has a radiopaque cap. The foams are not coupled to each other. FIG. 5D shows at least four foams deployed along with a pushing element resident within the delivery conduit. FIG. 5E shows more than ten foams deployed. For example, in an embodiment a single delivery conduit may come preloaded with five foams. To deploy ten foams a user may utilize two deliver conduit foam systems. FIG. 5F shows many deployed foams as well as the AAA stent graft. FIG. 5G shows how a AAA stent graft is not impinged upon by the relatively gentle expansion of foam. Notably the diameter of the graft remains largely unchanged between before and after foam deployment images.

Images 5A-F show an ability for embodiments to be delivered using minimally invasive techniques, the low density nature of the material to not add weight to the vulnerable region, and the ability of the materials to conform to the surrounding environment to minimize damage to surrounding tissues and structures.

This is in contrast to some conventional systems. Such systems show that the material used to fill the void space provided substantial added mass to the stent graft system, which resulted in graft migration due to gravitational effects of the material mass. There have also been issues with embolic material migration out of the "endobag" which contains the material due to fracture in the endobag. There have been deaths reported and adverse events as a result of the observations. The use of such conventional technologies (e.g., embolic coils or glues) also achieve a lesser result as substantially large numbers of coils are required to fill the space, resulting in greatly increased procedural costs and the same risk of added mass to a vulnerable region in vivo.

Embodiments include foam devices where each of the devices includes a proximal marker band (e.g., a radio opaque band that adheres to a proximal end of the foam using an adhesive.) Such foams may not include a filament or wire that traverse the length of the foam. This may include 2 to 10 foam plugs loaded into an introducer (delivery conduit). Embodiments include 2, 3, 4, 5, 6, 7, 8 or more plugs in a delivery conduit. The plugs or foam portions may not be permanently coupled to each other (e.g., they are merely adjacent one another in the delivery conduit but nothing tethers or binds them together once they deploy from the conduit). However, in other embodiments the foams may be crimped over a wire (which may or may not be coiled), such as a wire made from platinum and/or iridium. In other embodiments the foams are crimped over a length of suture, such as polypropylene suture. Other embodiments may include foams crimped over a shape memory material, such as a length of nitinol (e.g., 0.0065" in diameter).

In an embodiment the polymer backbone of the SMP foam is modified with linkages that degrade over time in the presence of water or oxidative species to create small molecules that can be cleared by the body. This creates a biodegradable implant that leaves only native scar tissue in the patient's body, which is not possible with any current endoleak treatments.

An embodiment includes a SMP foam synthesized using polyfunctional alcohols (triethanolamine and N,N,N',N'-Tetrakis(2-hydroxypropyl)ethylenediamine), diisocyanate monomers (triemethylhexamethylene diisocyanate, hexamethylene diisocyanate, Isophorone diisocyanate), blowing agents, surfactants, and catalysts. Polyfunctional alcohols containing water labile linkages such as anhydride or ester linkages could also be included in the foam to facilitate hydrolytic biodegradation. Alternatively, monomers can include tertiary amines or ether linkages to facilitate oxidative biodegradation. The foam is doped with radio-opaque particles during the foaming process to facilitate visualization under fluoroscopy during endovascular placement. The foam components are homogeneously mixed and cured in an oven. After polymerization, the foam is post processed into the appropriate device shape.

In an embodiment the SMP foams are crimped and attached to a delivery system. Several foam devices are inserted into the AAA sac via the delivery system which navigates the foams through catheters placed within the aneurysm sac during the stent graft placement. Once the implant is properly placed, the delivery system provides a stimulus to expand the foam. This stimulus could be heated saline or solvent that plasticizes the foam and causes it to expand. Heated saline or solvent may also be pumped through the delivery catheter. Alternatively, natural body temperature may serve as the stimulus for foam actuation. The expanded foam devices will fill the aneurysm volume between the stent graft and aneurysm wall.

Another embodiment utilizes the foam, fabricated as described above, as an enhancement to existing stent grafts. In this case, SMP foam would be wrapped and crimped around the stent graft. The foam is fixed to the graft material with an adhesive, or woven into the mesh network of the stent. The foam geometry may be a single annulus of bulk foam, or segmented "scale" geometries that facilitate a small cross section after device crimping. Segmented foam sections may also help minimize foam folding and strain during stent delivery and deployment prior to the SMP foam actuation.

Example 1b. A system comprising: a flexible conduit; first, second, and third open-cell, polyurethane, thermoset, shape memory polymer (SMP) foams simultaneously included within the flexible conduit; a flexible rod.

Even though this embodiment includes at least 3 SMP foams, other embodiments may include a single SMP foam. For example, an embodiment includes a single foam plug for biopsy occlusion. The physician removes a piece of tissue (e.g., biopsies a kidney, liver, or lung) and then pushes a crimped SMP foam (e.g., shaped like a rod) through the biopsy needle into the biopsy tissue track. Such a foam may include a marker band on its proximal end and the marker band will sit flush with the organ surface once implanted.

Another embodiment may omit the flexible rod. For example, the conduit SMP foams may be included in a kit and the kit may not include the flexible rod. Instead, a physician may use some other rod from outside the kit to advance the SMP foams from the conduit.

Even though this embodiment includes at least 3 SMP foams, other embodiments may include 1, 2, 4, 5 or more SMP foams within the conduit.

Such a "flexible conduit" may include an introducer.

Example 2b. The system of example 1b wherein: the flexible conduit includes a proximal third, a middle third, and a distal third; the first, second, and third SMP foams are simultaneously included in the distal third of the flexible conduit.

Example 3b. The system of example 2b wherein the first, second, and third SMP foams are not fixedly coupled to each other.

Example 4b. The system of example 2b wherein the first, second, and third SMP foams are configured to deploy from the flexible conduit such that they are not fixedly secured to one another immediately after their collective deployment from the flexible conduit.

Example 5b. The system of example 2b wherein: in a first orientation the first, second, and third SMP foams are included in the distal third of the flexible conduit; in the first orientation the first, second, and third SMP foams are coupled to each other via the flexible conduit but are not fixedly coupled to each other; in a second orientation the first, second, and third SMP foams are not coupled to each other after they are deployed from the flexible conduit.

Another version of Example 5b. The system of example 1b wherein: in a first orientation the first, second, and third SMP foams are substantially evenly spaced throughout proximal, middle, and distal thirds of the flexible conduit; in the first orientation the first, second, and third SMP foams are coupled to each other via the flexible conduit but are not fixedly coupled to each other; in a second orientation the first, second, and third SMP foams are not coupled to each other after they are deployed from the flexible conduit.

Example 6b. The system of example 2b wherein the first, second, and third SMP foams are configured to deploy from the flexible conduit in serial fashion such that the first SMP foam deploys from the flexible conduit before the second SMP foam and the second SMP foam deploys form the flexible conduit before the third SMP foam.

Example 7b. The system according to any of examples 1b-6b wherein: the first, second, and third SMP foams respectively include first, second, and third metal portions; each of the first, second, and third SMP foams includes a long axis; the first SMP foam includes a proximal third, a middle third, and a distal third; a first plane, which is orthogonal to the long axis of the first SMP, which intersects the first metal portion and the proximal third of first SMP foam; the first metal portion does not extend to the middle and distal thirds of the first SMP foam.

Example 8b. The system of example 7b wherein: the first SMP foam includes a second plane, which is orthogonal to the long axis of the first SMP, which intersects the middle third of first SMP foam but not any portion of the first metal portion; and the first SMP foam includes no backbone extending beyond the first metal portion.

Another version of Example 8b. The system of example 7b wherein: the first SMP foam includes a second plane, which is orthogonal to the long axis of the first SMP, which intersects the middle third of first SMP foam but not any portion of the first metal portion; and an outer perimeter of the first SMP foam intersects the second plane to form a single closed perimeter; only SMP foam is included within the single closed perimeter.

Another version of Example 8b. The system of example 7b wherein: the first SMP foam includes a second plane, which is orthogonal to the long axis of the first SMP, which intersects the middle third of the first SMP foam but not any portion of the first metal portion; and the first SMP foam may include a radiopaque backbone extending beyond the first metal portion.

The radiopaque backbone may be comprised of, for example, one or more of the following: platinum, tantalum, iridium, tungsten, polyurethane doped with metallic nanoparticles Another version Example 8b. The system of example 7b wherein: the first SMP foam includes a second plane, which is orthogonal to the long axis of the first SMP, which intersects the middle third of first SMP foam but not any portion of the first metal portion; and an outer perimeter of the first SMP foam intersects the second plane to form a single closed perimeter; SMP foam and a radiopaque backbone is included within the single closed perimeter.

Example 9b. The system of example 2b wherein the first, second, and third SMP foams are fixedly coupled to each other.

Example 10b. The system of example 9b wherein a monolithic length of material extends through the first, second, and third SMP foams to couple the first, second, and third SMP foams to one another.

Example 11b. The system of example 10b wherein the monolithic length of material includes at least one of a polymer and a metal.

Another version of Example 11b. The system of example 11b wherein the monolithic length of material includes a filament.

As used herein a filament includes a slender threadlike object or fiber. For example, a filament may include a thin metal wire or a thread made from a polymer.

Another version of Example 11b. The system of example 1b wherein each of the first, second, and third SMP foams are (a) crimped, and (b) between 0 and 3 mm in diameter when crimped and between 8 and 30 mm in diameter when actuated into their primary state.

Another version of Example 11b. The system of example 1b wherein each of the first, second, and third SMP foams are (a) crimped, and (b) between 0 and 3 mm in diameter when crimped and between 3 and 30 mm in diameter when actuated into their primary state.

In other embodiments the crimped diameter is between 0 and 2 mm, 0 and 4 mm, 0 and 5 mm, or more. In other embodiments the actuated diameter is between 2 and 30 mm, 2 and 40, 2 and 50 mm, or more.

Another version of Example 11b. The system of example 1 wherein: the first SMP foam is covalently bonded to iodine; the first SMP foam is configured to expand from a compressed secondary state to an expanded primary state in response to thermal stimulus, and the first SMP foam is a poly(urethane-urea-amide).

Example 11c. The system of example 11b wherein the SMP foam is radiopaque.

Example 11d. The system according to any of examples 11b-11c wherein the iodine is included in a triiodobenzene monomer.

Example 11e. The system of example 11d wherein the triiodobenzene monomer includes at least one of (a) 5-amino-2,4,6-triiodoisophthalic acid (ATIPA), (b) diatrizoic acid, (c) iohexol, and (d) triiodophenol.

Example 12b. A method comprising: reacting a polyol with an isocyanate to form a reaction product; mixing the reaction product with a blowing agent to form an open-cell, polyurethane, thermoset, shape memory polymer (SMP) foam; forming first, second, and third SMP foams from the SMP foam; coupling radiopaque materials to proximal portions of each of the first, second, and third SMP foams; including the first, second, and third SMP foams simultaneously within a distal third of a flexible conduit; after including the first, second, and third SMP foams simultaneously within a distal third of a flexible conduit, sealing the flexible conduit and the first, second, and third SMP foams within a hermetically sealed storage container.

Example 13b. The method of example 12b wherein: the polyol includes at least one of triethanolamine (TEA), diethanolamine, butane diol, butyne diol, N,N,N',N' tetrakis (hydroxyl propylene) ethylenediamine (HPED), and combinations thereof; and the isocyanate includes at least one of hexamethylene diisocyanate (HDI), trimethyl hexamethylene diisocyanate (TMHDI), isophorone diisocyanate (IPDI), and combinations thereof.

Another version of Example 13b includes: The method of example 12 wherein: the polyol includes at least one of triethanolamine (TEA), diethanolamine, butane diol, N,N,N',N' tetrakis (hydroxyl propylene) ethylenediamine (HPED), and combinations thereof; and the isocyanate includes at least one of hexamethylene diisocyanate (HDI), trimethyl hexamethylene diisocyanate (TMHDI), isophorone diisocyanate (IPDI), and combinations thereof.

Example 14b. The method of example 13b, wherein the isocyanate includes at least 85% HDI.

Example 15b. The method of example 14b, wherein the isocyanate includes at least 95% HDI.

Example 16b. The method according to any of examples 13b-15b wherein the polyol includes at least 70% TEA.

Example 17b. The method according to example 16b wherein the polyol includes at least 80% TEA.

Example 18b. The method according to any of examples 12b-17b wherein the first SMP foam includes metal nanoparticles.

Embodiments for Examples 1b through 11e include a flexible conduit. However, other embodiments are not so limited.

Example 19b. A system comprising: a conduit; first, second, and third open-cell, polyurethane, thermoset, shape memory polymer (SMP) foams simultaneously included within the flexible conduit.

The conduit may be stiff, like a needle. For example, the first, second, and third SMP foams (and fourth, fifth SMP foams or more) could be preloaded into such a needle and then delivered to an aneurysm sac via translumbar puncture with the needle. A rod could be forced through the needle to deploy the foams. Thus, embodiments allow for the examples 1 to 11g to have such a stiff conduit substituted for the flexible conduit.

An embodiment includes flexible conduit and a stiff needle. The flexible conduit is pushed through the needle. The flexible conduit includes one or more SMP foams which may be deployed from the needle using a pusher element.

Embodiments may have SMP foams subjected to plasma surface treatments, changes in monomers, and the incorporation of water labile linkages into the polymer backbone that biodegrade via hydrolysis. Tissue ingrowth could be stimulated by the bulk or surface chemistry of the implant, or by initial thermal or chemical stimulus to the endothelium from the foam actuation mechanism.

Example 1c. A system comprising: a flexible conduit that simultaneously includes: (a) a first open-cell, polyurethane, thermoset, shape memory polymer (SMP) foam; (b) a second open-cell, polyurethane, thermoset, SMP foam; and (c) a third open-cell, polyurethane, thermoset, SMP foam; wherein (a) the first SMP foam includes first and second ends that oppose each other, (b) the second SMP foam includes first and second ends that oppose each other, and (c) the third SMP foam includes first and second ends that oppose each other; wherein (a) the first SMP foam includes a first backbone that extends from the first end of the first SMP foam to the second end of the first SMP foam; (b) the second SMP foam includes a second backbone that extends from the first end of the second SMP foam to the second end of the second SMP foam; (a) the third SMP foam includes a third backbone that extends from the first end of the third SMP foam to the second end of the third SMP foam; wherein (a) the first, second, and third SMP foams are not fixedly coupled to each other; (b) the first, second, and third SMP foams are configured to deploy from the flexible conduit such that they are not fixedly secured to one another immediately after their collective deployment from the flexible conduit, and (c) the first, second, and third SMP foams are configured to deploy from the flexible conduit in serial fashion such that the first SMP foam deploys from the flexible conduit before the second SMP foam and the second SMP foam deploys form the flexible conduit before the third SMP foam; wherein (a) the first backbone includes at least one of platinum, tantalum, iridium, tungsten, or polyurethane, (b) the second backbone includes at least one of platinum, tantalum, iridium, tungsten, or polyurethane, (c) the third backbone includes at least one of platinum, tantalum, iridium, tungsten, or polyurethane; wherein (a) the first SMP foam is between 0 and 3 mm in diameter, (b) the second SMP foam is between 0 and 3 mm in diameter, and (c) the third SMP foam is between 0 and 3 mm in diameter.

As used herein, a "flexible conduit" may have the flexibility of an introducer made from a polymer, such as polyether ether ketone (PEEK). However, a "rigid conduit" may have the flexibility of a metal biopsy needle of 15-19 gauge.

Example 2c. The system of example 1c wherein: (a) the first backbone includes a monolithic length of material that extends from the first end of the first SMP foam to the second end of the first SMP foam, (b) the second backbone includes a monolithic length of material that extends from the first end of the second SMP foam to the second end of the second SMP foam, and (c) the third backbone includes a monolithic length of material that extends from the first end of the third SMP foam to the second end of the third SMP foam.

Example 3c. The system of example 2c wherein the monolithic length of material of the first backbone includes at least one of a filament and a coil.

Example 4c. The system of example 3c wherein the first SMP foam includes: (a) at least one of Hexamethylene Diisocyanate (HDI) or Trimethyl Hexamethylene Diisocyanate (TMHDI), and (b) at least one of N,N,N',N'-Tetrakis (2-Hydroxypropyl)ethylenediamine (HPED) or Triethanolamine (TEA).

Such a foam may be degradable.

Another version of Example 4c. The system of example 3c wherein the first SMP foam includes a reaction product of: (a) at least one of Hexamethylene Diisocyanate (HDI) or Trimethyl Hexamethylene Diisocyanate (TMHDI), and (b) at least one of N,N,N',N'-Tetrakis(2-Hydroxypropyl)ethylenediamine (HPED) or Triethanolamine (TEA).

Example 5c. The system of example 3c wherein the first SMP foam includes: (a) at least one of Hexamethylene Diisocyanate (HDI) or Trimethyl Hexamethylene Diisocyanate (TMHDI), and (b) at least one of Glycerol; 1,2,6-hexanetriol (HT); 3-methyl-1,5-pentanediol (MPD); or 2-butyl-2-ethyl propanediol (BEP).

For example, the foam may be formed from HDI and HT monomers. Those monomers react before polymerization is complete. However, as used herein, such a polymer foam would be said to include HDI and HT.

Such a foam may be non-degradable and mechanically tougher than the foam of Example 4c.

Another version of Example 5c. The system of example 3c wherein the first SMP foam includes: a reaction product of (a) at least one of Hexamethylene Diisocyanate (HDI) or Trimethyl Hexamethylene Diisocyanate (TMHDI), and (b) at least one of Glycerol; 1,2,6-hexanetriol (HT); 3-methyl-1,5-pentanediol (MPD); or 2-butyl-2-ethyl propanediol (BEP).

Example 6c. The system of example 3c wherein the first SMP foam includes: (a) at least one of Hexamethylene Diisocyanate (HDI) or Trimethyl Hexamethylene Diisocyanate (TMHDI), (b) at least one of Glycerol; 1,2,6-hexanetriol (HT); 3-methyl-1,5-pentanediol (MPD); or 2-butyl-2-ethyl propanediol (BEP), and (c) at least one of 5-amino-2,4,6-triiodoisophthalic acid (ATIPA), Iohexol, or Triiodophenol.

Another version of Example 6c. The system of example 3c wherein the first SMP foam includes a reaction product of: (a) at least one of Hexamethylene Diisocyanate (HDI) or Trimethyl Hexamethylene Diisocyanate (TMHDI), (b) at least one of Glycerol; 1,2,6-hexanetriol (HT); 3-methyl-1, 5-pentanediol (MPD); or 2-butyl-2-ethyl propanediol (BEP), and (c) at least one of 5-amino-2,4,6-triiodoisophthalic acid (ATIPA), Iohexol, or Triiodophenol.

Such a foam may be x-ray visible, non-degradable and mechanically tougher than the foam of Example 4c.

Example 6c'. A method comprising: reacting a polyol with an isocyanate to form a reaction product; mixing the reaction product with a blowing agent to form an open-cell, polyurethane, thermoset, shape memory polymer (SMP) foam according to any of examples 4c, 5c, 6c; forming first, second, and third SMP foams from the SMP foam; including the first, second, and third SMP foams simultaneously within a conduit; after including the first, second, and third SMP foams simultaneously within the conduit, sealing the conduit and the first, second, and third SMP foams within a hermetically sealed storage container.

Example 7c. The system of example 3c wherein (a) the first SMP foam has a length between 7 mm and 25 mm, (b) the second SMP foam has a length between 7 mm and 25 mm, and (c) the third SMP foam has a length between 7 mm and 25 mm.

Applicant determined this to be a critical range for some embodiments. Foams shorter than 7 mm exhibit undesirable occlusion and foams longer than 25 mm are overly rigid and difficult to maneuver through tortuous vasculature.

Example 8c. The system of example 7c wherein: the flexible conduit includes a length; the first, second, and third SMP foams are collectively distributed across more than a third of the length of the flexible conduit.

Example 9c. The system of example 1c wherein: the first SMP foam is covalently bonded to iodine; the first SMP foam is configured to expand from a compressed secondary state to an expanded primary state in response to thermal stimulus, and the first SMP foam is a poly(urethane-urea-amide).

Another version of Example 9c. The system of example 1c wherein: the first SMP foam is covalently bonded to iodine; and the first SMP foam is configured to expand from a compressed secondary state to an expanded primary state in response to thermal stimulus.

Example 10c. The system of example 9c wherein the SMP foam is radiopaque.

Example 11c. The system of example 9c wherein the iodine is included in a triiodobenzene monomer.

Another version of Example 11c. The system of example 9c wherein the iodine is a reaction product of a triiodobenzene monomer.

Example 12c. The system of example 11c wherein the triiodobenzene monomer includes at least one of (a) 5-amino-2,4,6-triiodoisophthalic acid (ATIPA), (b) diatrizoic acid, (c) iohexol, or (d) triiodophenol.

Example 13c. The system of example 1c wherein: in a first orientation the first, second, and third SMP foams are coupled to each other via the flexible conduit but are not fixedly coupled to each other; in a second orientation the first, second, and third SMP foams are not coupled to each other after they are deployed from the flexible conduit.

Example 14c. A system comprising: a flexible conduit that includes an open-cell, polyurethane, thermoset, shape memory polymer (SMP) foam; wherein the SMP foam is between 0 and 3 mm in diameter.

For instance, the 0 and 3 mm range is critical in that for certain embodiments the foam must have a structure that allows for such compressions such that the foam can be deployed via a catheter (e.g., 5F) and through tortuous vasculature. This separates foams described herein from many conventional embolic materials.

Another version of Example 14c. A system comprising: a flexible conduit that includes an open-cell, polyurethane, thermoset, shape memory polymer (SMP) foam; wherein the SMP foam is between 0 and 3 mm in diameter; wherein the SMP foam includes first and second cells which directly contact each other; wherein (a)(i) the first and second cells share and directly contact a ring of struts that provide structural support for the first and second cells, (a)(ii) a membrane directly contacts the ring of struts, and (a)(iii) the membrane is partially reticulated but not fully reticulated; wherein the partially reticulated membrane includes: (b)(i) a void that forms a path configured to allow fluid to flow between the first and second cells, (b)(ii) an interface, between the partially reticulated membrane and the void, which is rough and uneven; wherein the foam includes cells, including the first and second cells, which are anisotropic in shape and have unequal major and minor axes; wherein: (a) the ring of struts defines an outer perimeter of the membrane and the void defines an inner perimeter of the membrane; (b) an outer membrane area for the membrane is an area bounded by the outer perimeter defining an area of the membrane before reticulation; (c) a void area is an area bounded by the inner perimeter defining an area of the void; and (d) the void area is between 25% and 75% of the outer membrane area.

Example 15c. The system of example 14c wherein the SMP foam includes: (a) at least one of Hexamethylene Diisocyanate (HDI) or Trimethyl Hexamethylene Diisocyanate (TMHDI), and (b) at least one of Glycerol; 1,2,6-hexanetriol (HT); 3-methyl-1,5-pentanediol (MPD); or 2-butyl-2-ethyl propanediol (BEP).

Another version of Example 15c. The system of example 14c wherein the SMP foam includes a reaction product of: (a) at least one of Hexamethylene Diisocyanate (HDI) or Trimethyl Hexamethylene Diisocyanate (TMHDI), and (b) at least one of Glycerol; 1,2,6-hexanetriol (HT); 3-methyl-1,5-pentanediol (MPD); or 2-butyl-2-ethyl propanediol (BEP).

Example 16c. The system of example 14c wherein the SMP foam includes: (a) at least one of Hexamethylene Diisocyanate (HDI) or Trimethyl Hexamethylene Diisocyanate (TMHDI), (b) at least one of Glycerol; 1,2,6-hexanetriol (HT); 3-methyl-1,5-pentanediol (MPD); or 2-butyl-2-ethyl propanediol (BEP), and (c) at least one of 5-amino-2,4,6-triiodoisophthalic acid (ATIPA), Iohexol, or Triiodophenol.

Another version of Example 16c. The system of example 14c wherein the SMP foam includes a reaction product of: (a) at least one of Hexamethylene Diisocyanate (HDI) or Trimethyl Hexamethylene Diisocyanate (TMHDI), (b) at least one of Glycerol; 1,2,6-hexanetriol (HT); 3-methyl-1,5-pentanediol (MPD); or 2-butyl-2-ethyl propanediol (BEP), and (c) at least one of 5-amino-2,4,6-triiodoisophthalic acid (ATIPA), Iohexol, or Triiodophenol.

Example 17c. The system of example 14c wherein the SMP foam is: covalently bonded to iodine; configured to expand from a compressed secondary state to an expanded primary state in response to thermal stimulus; and a poly (urethane-urea-amide).

Example 18c. The system of example 17c wherein the SMP foam is radiopaque.

Example 19c. The system of example 17c wherein the iodine is included in a triiodobenzene monomer.

Example 20c. The system of example 19c wherein the triiodobenzene monomer includes at least one of (a) 5-amino-2,4,6-triiodoisophthalic acid (ATIPA), (b) diatrizoic acid, (c) iohexol, or (d) triiodophenol.

Example 21c. The system of example 14c wherein: the SMP foam includes a plane, which is orthogonal to a long axis of the SMP foam and which intersects a middle third of the SMP foam; an outer perimeter of the SMP foam intersects the second plane to form a single closed perimeter; only SMP foam is included within the single closed perimeter.

Such a system includes no backbone.

Example 22c. A system comprising: a stiff conduit that includes an open-cell, polyurethane, thermoset, shape memory polymer (SMP) foam; wherein the SMP foam is between 0 and 3 mm in diameter; wherein the SMP foam includes first and second cells which directly contact each other; wherein (a)(i) the first and second cells share and directly contact a ring of struts that provide structural support for the first and second cells, (a)(ii) a membrane directly contacts the ring of struts, and (a)(iii) the membrane is partially reticulated but not fully reticulated; wherein the partially reticulated membrane includes: (b)(i) a void that forms a path configured to allow fluid to flow between the first and second cells, (b)(ii) an interface, between the partially reticulated membrane and the void, which is rough and uneven; wherein the foam includes cells, including the first and second cells, which are anisotropic in shape and have unequal major and minor axes; wherein: (a) the ring of struts defines an outer perimeter of the membrane and the void defines an inner perimeter of the membrane; (b) an outer membrane area for the membrane is an area bounded by the outer perimeter defining an area of the membrane before reticulation; (c) a void area is an area bounded by the inner perimeter defining an area of the void; and (d) the void area is between 25% and 75% of the outer membrane area.

The stiff conduit may be used as a biopsy needle.

Example 23c. A system comprising: a stiff conduit that simultaneously includes: (a) a first open-cell, polyurethane, thermoset, shape memory polymer (SMP) foam; (b) a second open-cell, polyurethane, thermoset, SMP foam; and (c) a third open-cell, polyurethane, thermoset, SMP foam; wherein (a) the first SMP foam includes first and second ends that oppose each other, (b) the second SMP foam includes first and second ends that oppose each other, and (c) the third SMP foam includes first and second ends that oppose each other; wherein (a) the first SMP foam includes a first backbone that extends from the first end of the first SMP foam to the second end of the first SMP foam; (b) the second SMP foam includes a second backbone that extends from the first end of the second SMP foam to the second end of the second SMP foam; (a) the third SMP foam includes a third backbone that extends from the first end of the third SMP foam to the second end of the third SMP foam; wherein (a) the first, second, and third SMP foams are not fixedly coupled to each other; (b) the first, second, and third SMP foams are configured to deploy from the stiff conduit such that they are not fixedly secured to one another immediately after their collective deployment from the stiff conduit, and (c) the first, second, and third SMP foams are configured to deploy from the stiff conduit in serial fashion such that the first SMP foam deploys from the stiff conduit before the second SMP foam and the second SMP foam deploys form the stiff conduit before the third SMP foam; wherein (a) the first backbone includes at least one of platinum, tantalum, iridium, tungsten, or polyurethane, (b) the second backbone includes at least one of platinum, tantalum, iridium, tungsten, or polyurethane, (c) the third backbone includes at least one of platinum, tantalum, iridium, tungsten, or polyurethane; wherein (a) the first SMP foam is between 0 and 3 mm in diameter, (b) the second SMP foam is between 0 and 3 mm in diameter, and (c) the third SMP foam is between 0 and 3 mm in diameter.

The stiff conduit may be used as a biopsy needle.

Example 24c: A method comprising: implant a stent and a wire within an aneurysm; place a conduit over the wire; deliver a SMP foam via the catheter, wherein the SMP via includes the first SMP foam of Example 1c; expand the SMP foam to conform the SMP foam to the aneurysm wall.

Example 25c: A method comprising: implant a stent and a wire within an aneurysm; place a conduit over the wire; deliver a SMP foam via the catheter, wherein the SMP via includes the SMP foam of Example 14c; expand the SMP foam to conform the SMP foam to the aneurysm wall.

Example 26c: A method comprising: implant a stent and a wire within an aneurysm; place a conduit over the wire; deliver a SMP foam via the catheter, wherein the SMP via includes the first SMP foam according to any of Examples 4c, 5c, 6c; expand the SMP foam to conform the SMP foam to the aneurysm wall.

Example 27c: A method comprising: implant a stent and a wire within an aneurysm; place a conduit over the wire; deliver a SMP foam via the catheter, wherein the SMP via includes the SMP foam according to any of Examples 15c, 16c, 17c, 18c, 19c, 20c; expand the SMP foam to conform the SMP foam to the aneurysm wall.

Example 28c. A method comprising: reacting a polyol with an isocyanate to form a reaction product; mixing the reaction product with a blowing agent to form an open-cell, polyurethane, thermoset, shape memory polymer (SMP) foam according to any of examples 15c, 16c, 17c, 18c, 19c, 20c; including the SMP foam within a conduit; after including the SMP foam within the conduit, sealing the conduit and the SMP foam within a hermetically sealed storage container.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

The invention claimed is:

1. A method comprising:
   implant a stent graft and a wire within a patient and adjacent one another;
   advance a first conduit over the wire and into the patient;
   insert a second conduit into the first conduit, wherein within the second conduit: (a) first, second, and third open-cell, polyurethane, thermoset, shape memory polymer (SMP) foams are simultaneously disposed; and (b) the first, second, and third SMP foams are arranged serially with respect to each other and are not fixedly coupled to each other;
   deploy the first SMP foam from the first conduit and into the patient at a first location;
   after deploying the first SMP foam, deploy the second SMP foam from the first conduit and into the patient at a second location; and
   after deploying the second SMP foam, deploy the third SMP foam from the first conduit and into the patient at a third location;
   wherein (a)(i) a first plane, orthogonal to a long axis of the first SMP foam, intersects both a proximal half of the first SMP foam and a first metal structure that is coupled to the first SMP foam; (a)(ii) an additional first plane, parallel to the first plane, intersects a distal half of the first SMP foam but does not intersect the first metal structure, (b)(i) a second plane, orthogonal to a long axis of the second SMP foam, intersects both a proximal half of the second SMP foam and a second metal structure that is coupled to the second SMP foam; (b)(ii) an additional second plane, parallel to the second plane, intersects a distal half of the second SMP foam but does not intersect the second metal structure, (c)(i) a third plane, orthogonal to a long axis of the third SMP foam, intersects both a proximal half of the third SMP foam and a third metal structure that is coupled to the third SMP foam; (c)(ii) an additional third plane, parallel to the third plane, intersects a distal half of the third SMP foam but does not intersect the third metal structure.

2. The method of claim 1, wherein (a) the first metal structure includes at least one of platinum, tantalum, iridium, tungsten, or combinations thereof, (b) the second metal structure includes at least one of platinum, tantalum, iridium, tungsten, or combinations thereof, (c) the third metal structure includes at least one of platinum, tantalum, iridium, tungsten, or combinations thereof.

3. The method of claim 2, wherein (a) the first SMP foam, in an unexpanded state, is between 0 and 3 mm in diameter measured orthogonal to the long axis of the first SMP foam, (b) the second SMP foam, in an unexpanded state, is between 0 and 3 mm in diameter measured orthogonal to the long axis of the second SMP foam, and (c) the third SMP foam, in an unexpanded state, is between 0 and 3 mm in diameter measured orthogonal to the long axis of the third SMP foam.

4. The method of claim 2 comprising using at least one of the wire or a pushing element to push each of the first, second, and third SMP foams out of the first conduit and into the patient.

5. The method of claim 2 comprising:
   after deploying the first SMP foam, relocating the first conduit before deploying the second SMP foam from the first conduit and into the patient at the second location; and
   after deploying the second SMP foam, relocating the first conduit before deploying the third SMP foam from the first conduit and into the patient at the third location.

6. The method of claim 2 wherein the first, second, and third locations are within an abdominal aortic aneurysm (AAA).

7. The method of claim 2 wherein:
   an outer perimeter of the first SMP foam is included entirely within the additional first plane to form a single closed perimeter; and
   only SMP foam is included within the single closed perimeter.

8. The method of claim 2 comprising:
   obtaining a fluoroscopic image of the first, second, and third SMP foams; and
   ascertaining locations of the first, second, and third SMP foams within the fluoroscopic image based on ascertaining locations of the first, second, and third metal structures within the fluoroscopic image.

9. The method of claim 8 comprising obtaining the fluoroscopic image of the first, second, and third SMP foams while the first SMP foam is deployed from the first conduit but the third SMP foam remains within the first conduit.

10. The method of claim 2, wherein each of the first, second, and third SMP foams are configured to expand in response to thermal stimulus, exposure to blood, or combinations thereof.

11. The method of claim 10, wherein the first SMP foam is a poly(urethane-urea-amide).

12. The method of claim 10, wherein the first SMP foam includes a hydrolytically degradable ester linkage.

13. The method of claim 1:
   wherein a fourth SMP foam is simultaneously disposed within the second conduit with the first, second, and third SMP foams;
   the method further comprising removing the first conduit from the patient after deploying the first SMP foam from the first conduit and into the patient at the first location but while the fourth SMP foam is still located in one of the first conduit, the second conduit, or combinations thereof.

14. The method of claim 1 comprising implanting the stent graft into the patient after implanting the wire into the patient.

15. A method comprising:
   insert a conduit into a patient, wherein within the conduit: (a) first, second, and third open-cell, polyurethane, thermoset, shape memory polymer (SMP) foams are simultaneously disposed; and (b) the first, second, and third SMP foams are arranged serially with respect to each other and are not fixedly coupled to each other;

deploy the first SMP foam from the conduit and into the patient at a first location;

after deploying the first SMP foam, deploy the second SMP foam from the conduit and into the patient at a second location; and after deploying the second SMP foam, deploy the third SMP foam from the conduit and into the patient at a third location;

wherein (a)(i) a first plane, orthogonal to a long axis of the first SMP foam, intersects a first metal structure that is connected to a proximal half of the first SMP foam; (a)(ii) an additional first plane, parallel to the first plane, intersects a distal half of the first SMP foam but does not intersect the first metal structure, (b)(i) a second plane, orthogonal to a long axis of the second SMP foam, intersects a second metal structure that is connected to a proximal half of the second SMP foam; (b)(ii) an additional second plane, parallel to the second plane, intersects a distal half of the second SMP foam but does not intersect the second metal structure, (c)(i) a third plane, orthogonal to a long axis of the third SMP foam, intersects a third metal structure that is connected to a proximal half of the third SMP foam; (c)(ii) an additional third plane, parallel to the third plane, intersects a distal half of the third SMP foam but does not intersect the third metal structure.

16. The method of claim 15:

wherein (a) the first metal structure includes at least one of platinum, tantalum, iridium, tungsten, or combinations thereof, (b) the second metal structure includes at least one of platinum, tantalum, iridium, tungsten, or combinations thereof, (c) the third metal structure includes at least one of platinum, tantalum, iridium, tungsten, or combinations thereof;

wherein (a) the first SMP foam, in an unexpanded state, is between 0 and 3 mm in diameter measured orthogonal to the long axis of the first SMP foam, (b) the second SMP foam, in an unexpanded state, is between 0 and 3 mm in diameter measured orthogonal to the long axis of the second SMP foam, and (c) the third SMP foam, in an unexpanded state, is between 0 and 3 mm in diameter measured orthogonal to the long axis of the third SMP foam.

17. The method of claim 16 wherein the first, second, and third locations are within a peripheral blood vessel.

18. The method of claim 17 comprising:

obtaining a fluoroscopic image of the first, second, and third SMP foams; and ascertaining locations of the first, second, and third SMP foams within the fluoroscopic image based on ascertaining locations of the first, second, and third metal structures within the fluoroscopic image.

19. The method of claim 18 comprising obtaining the fluoroscopic image of the first, second, and third SMP foams while the first SMP foam is deployed from the conduit but the third SMP foam remains within the conduit.

20. The method of claim 16, wherein:

each of the first, second, and third SMP foams are configured to expand in response to thermal stimulus, exposure to blood, or combinations thereof; and the first SMP foam includes a hydrolytically degradable ester linkage.

\* \* \* \* \*